(12) United States Patent
Paulsson et al.

US007781169B1

(10) Patent No.: US 7,781,169 B1
(45) Date of Patent: Aug. 24, 2010

(54) DIAGNOSIS OF GLUTEN SENSITIVE ENTEROPATHY AND OTHER AUTOIMMUNOPATHIES

(76) Inventors: Mats Paulsson, Institute for Biochemistry II, Medical Faculty, University of Cologne, Joseph-Stelzmann-Str. 52, D-50931 Cologne (DE); Uwe Odenthal, Institute for Biochemistry II, Medical Faculty, University of Cologne, Joseph-Stelzmann-Str. 52, D-50931 Cologne (DE); Neil Smyth, Institute for Biochemistry II, Medical Faculty, University of Cologne, Joseph-Stelzmann-Str. 52, D-50931 Cologne (DE); Daniel Aeschlimann, Dental School, University of Wales College of Medicine, Heath Park, Cardiff CF14 4X4 (GB); Sarolta Karpati, Department of Dermato-Venerology, Semmelweis University of Medicine, Maria u. 41, H-1085 Budapest (HU); Miklos Sardy, Department of Dermato-Venerology, Semmelweis University of Medicine, Maria u. 41, H-1085 Budapest (HU)

( * ) Notice: Subject to any disclaimer, the term of this patent is extended or adjusted under 35 U.S.C. 154(b) by 1102 days.

(21) Appl. No.: 10/019,067

(22) PCT Filed: Jun. 28, 2000

(86) PCT No.: PCT/EP00/06025
§ 371 (c)(1),
(2), (4) Date: Jun. 28, 2002

(87) PCT Pub. No.: WO01/01133
PCT Pub. Date: Jan. 4, 2001

(30) Foreign Application Priority Data
Jun. 28, 1999 (EP) ............................... 99111975.1

(51) Int. Cl.
*G01N 33/53* (2006.01)
(52) U.S. Cl. ..................... 435/7.1; 435/7.92; 436/501; 436/513; 436/811
(58) Field of Classification Search ................. 436/501, 436/506, 811; 435/6, 7.1, 7.92–7.95
See application file for complete search history.

(56) References Cited

U.S. PATENT DOCUMENTS 5,726,051 A 3/1998 Fraij et al. ................... 435/193
6,319,726 B1 * 11/2001 Schuppan et al. ........... 436/506

FOREIGN PATENT DOCUMENTS

DE 19630557 A1 1/1998

WO WO 98/03872 * 1/1998

OTHER PUBLICATIONS

Locke et al., IgA anti-tissue transglutaminase as a diagnostic marker of gluten sensitive enteropathy, Journal of Clinical Pathology 1999, 52: 274-277.*
Amin et al., Correlation between tissue transglutaminase antibodies and endomysium antibodies as diagnostic markers of coeliac disease, Clinica Chimica Acta 282 (Apr. 1999) 219-225.*
Bazzigaluppi et al., Comparison of Tissue Transglutaminase-Specific Antibody Assays with Established Antibody Measurements for Coeliac Disease, Journal of Autoimmunity (Feb. 1999) 12, 51-56.*
Web definitions, Google, differential diagnosis, Jul. 12, 2007.*
Dietrich, W. et al. Identification of tissue transglutaminase as the autoantigen of celiac disease. *Nature Med.* 1997;3(7):797-801.
Seissler, J. et al. Antibodies to human recombinant tissue transglutaminase measured by radioligand assay: evidence for high diagnostic sensitivity for celiac disease. *Horm. Metab. Res.* Jun. 1999;31(6):375-9.
Sardy, M. et al. Recombinant human tissue transglutaminase ELISA for the diagnosis of gluten-sensitive enteropathy. *Clin. Chem.* Dec. 1999;45(12):2142-9.
International Search Report to PCT/EP00/06025 (Jun. 28, 2000), 4 pages.
International Preliminary Examination Report for PCT/EP00/06025 (Jun. 28, 2000), 7 pages.
Andberg, M. et al. "Mutation of tyrosine 383 in leukotriene $A_4$ hydrolase allows conversion of leukotriene $A_4$ into 5S,6S-dihydroxy-7,9-trans-11,14-cis-eicosatetraenoic acid. Implications for the epoxide hydrolase mechanism," *J. Biol. Chem.* Sep. 12, 1997;272(37):23057-63.
Barrett, A.J. et al. Eds. "336. Introduction: family M1 of membrane alanyl aminopeptidase," in Handbook of proteolytic enzymes Oct. 1998; pp. 994-996.
Blomster, M. et al. "Evidence for a catalytic role of tyrosine 383 in the peptidase reaction of leukotriene $A_4$ hydrolase," *Eur. J. Biochem.* Aug. 1, 1995;231(3):528-34.

(Continued)

*Primary Examiner*—Melanie J Yu
*Assistant Examiner*—Gary W Counts
(74) *Attorney, Agent, or Firm*—Lahive & Cockfield, LLP; Jane E. Remillard, Esq.; Jill Gorny Sloper, Esq.

(57) ABSTRACT

Method for diagnosis of autoimmune diseases of the GSE-type or associated with gluten sensitive enteropathy comprising taking a sample and testing the sample for antibodies against human tissue transglutaminase, tissue-specific transglutaminases, or other transglutaminases. It was found that autoimmune diseases other than celiac disease can be diagnosed and distinguished in this way, notably, dermatitis herpetiformis Duhring, Crohn's disease, Addison's disease, AI hemolytic anemia, AI thrombocytopenic purpura, AI thyroid diseases, atrophic gastritis—pernicious anemia, IgA nephropathy or IgA glomerulonephritis, myasthenia gravis, partial lipodystrophy, polymyositis, primary biliary cirrhosis, primary sclerosing cholangitis, recurrent pericarditis, relapsing polychondritis, rheumatoid arthritis, rheumatism, sarcoidosis, Sjögren's syndrome, SLE, splenic atrophy, type I (insulin-dependent) diabetes mellitus, diabetes mellitus of other types, ulcerative colitis, vasculitis (both systemic and cutaneous), vitiligo as well as autoimmune diseases associated with infertility, increased risk of abortion, or reduced fetal growth.

1 Claim, 12 Drawing Sheets

OTHER PUBLICATIONS

Byrum, R.S. et al. "Determination of the contribution of cysteinyl leukotrienes and leukotriene $B_4$ in acute inflammatory responses using 5-lipoxygenase- and leukotriene $A_4$ hydrolase-deficient mice," *J. Immunol.* Dec. 15, 1999;163(12):6810-9.

Chen, X.-S. et al. "Role of leukotrienes revealed by targeted disruption of the 5-lipoxygenase gene," *Nature* Nov. 1994;372:179-182.

Crameri, A. et al. "DNA shuffling of a family of genes from diverse species accelerates directed evolution," *Nature* Jan. 15, 1998;391(6664):288-91.

Devchand, P.R. et al. "The PPARalpha-leukotriene $B_4$ pathway to inflammation control," *Nature* Nov. 7, 1996;384(6604):39-43.

Dittmann, K.H. et al. "MK-886, a leukotriene biosynthesis inhibitor, induces antiproliferative effects and apoptosis in HL-60 cells," *Leuk. Res.* Jan. 1998;22(1):49-53.

Drazen, J.M. et al. "Treatment of asthma with drugs modifying the leukotriene pathway," *N. Engl. J. Med.* Jan. 21, 1999;340(3):197-206.

Evans, J.F. "Leukotriene $A_3$. A poor substrate but a potent inhibitor of rat and human neutrophil leukotriene $A_4$ hydrolase," *J. Biol. Chem.* Sep. 15, 1985;260(20):10966-70.

Ford-Hutchinson, A.W. et al. "Leukotriene B, a potent chemokinetic and aggregating substance released from polymorphonuclear leukocytes," *Nature* Jul. 17, 1980;286:264-65.

Funk, C.D. et al. "Molecular cloning and amino acid sequence of leukotriene $A_4$ hydrolase," *Proc. Natl. Acad. Sci. USA* Oct. 1987;84(19):6677-81.

Griffiths, R.J. et al. "Leukotriene $B_4$ plays a critical role in the progression of collagen-induced arthritis," *Proc. Natl. Acad. Sci. USA* Jan. 17, 1995;92(2):517-21.

Griffiths, R.J. et al. "Collagen-induced arthritis is reduced in 5-lipoxygenase-activating protein-deficient mice," *J. Exp. Med.* Mar. 17, 1997;185(6):1123-9.

Haeggström, J.Z. et al. "Leukotriene $A_4$ hydrolase: structural and functional properties of the active center," *J. Lipid Mediat.* Mar.-Apr. 1993;6(1-3):1-13.

Hogg, J.H. et al. "Probing the activities and mechanisms of leukotriene $A_4$ hydrolase with synthetic inhibitors," *Chem. Eur. J.* 1998;4(9):1698-1713.

Kuchner, O. et al. "Directed evolution of enzyme catalysts," *Trends Biotechnol.* Dec. 1997;15(12):523-30.

Labaudinièere, R. et al. "ω-[(ω-Arylalkyl)thienyl]alkanoic acids: from specific $LTA_4$ hydrolase inhibitors to $LTB_4$ receptor antagonists," *J. Med. Chem.* Aug. 21, 1992;35(17):3170-9.

Lewis, R.A. et al. "Leukotrienes and other products of the 5-lipoxygenase pathway. Biochemistry and relation to pathobiology in human diseases," *N. Engl. J. Med.* Sep. 6, 1990;323(10):645-55.

Lorsch, J.R. et al. "In vitro evolution of new ribozymes with polynucleotide kinase activity," *Nature* Sep. 1, 1994;371(6492):31-6.

Medina, J.F. et al. "Leukotriene $A_4$ hydrolase: determination of the three zinc-binding ligands by site-directed mutagenesis and zinc analysis," *Proc. Natl. Acad. Sci. USA* Sep. 1, 1991;88(17):7620-4.

Ménard, A. et al. "The cytotoxic activity of *Bacillus anthracis* lethal factor is inhibited by leukotriene $A_4$ hydrolase and metallopeptidase inhibitors," *Biochem. J.* Dec. 1, 1996;320 ( Pt 2):687-91.

Mueller, M.J. et al. "Leukotriene $A_4$ hydrolase: mapping of a henicosapeptide involved in mechanism-based inactivation," *Proc. Natl. Acad. Sci. USA* Aug. 29, 1995;92(18):8383-7.

Mueller, M.J. et al. "Leukotriene $A_4$ hydrolase: protection from mechanism-based inactivation by mutation of tyrosine-378," *Proc. Natl. Acad. Sci. USA* Jun. 11, 1996;93(12):5931-5.

Mueller, M.J. et al. "Leukotriene $A_4$ hydrolase, mutation of tyrosine 378 allows conversion of leukotriene $A_4$ into an isomer of leukotriene $B_4$," *J. Biol. Chem.* Oct. 4, 1996;271(40):24345-8.

Nord, K. et al. "Binding proteins selected from combinatorial libraries of an alpha-helical bacterial receptor domain," *Nat. Biotechnol.* Aug. 1997;15(8):772-7.

Orning, L. et al: "Inhibition of leukotriene $A_4$ hydrolase/aminopeptidase by captopril," *J. Biol. Chem.* Sep. 5, 1991;266(25):16507-11.

Orning, L. et al. "The bifunctional enzyme leukotriene-$A_4$hydrolase is an arginine aminopeptidase of high efficiency and specificity," *J. Biol. Chem.* Apr. 15, 1994;269(15):11269-73.

Owman, C. et al. "The leukotriene $B_4$ receptor functions as a novel type of coreceptor mediating entry of primary HIV-1 isolates into CD4-positive cells," *PNAS. USA* Aug. 4, 1998;95(16):9530-4.

Rola-Pleszczynski, M. et al. "Leukotrienes augment interleukin 1 production by human monocytes," *J. Immunol.* Dec. 1985;135(6):3958-61.

Samuelsson, B. "Leukotrienes: mediators of immediate hypersensitivity reactions and inflammation," *Science* May 6, 1983;220(4597):568-75.

Samuelsson, B. et al. "Leukotrienes and lipoxins: structures, biosynthesis, and biological effects," *Science* Sep. 4, 1987;237(4819):1171-6.

Serhan, C.H. et al. "Lipid mediator networks in cell signaling: update and impact of cytokines," *FASEB J.* Aug. 1996;10:1-12.

Tsuge, H. et al. "Crystallization and preliminary X-ray crystallographic studies of recombinant human leukotriene $A_4$ hydrolase complexed with bestatin," *J. Mol. Biol.* May 20, 1994;238(5):854-6.

Vallee, B.L. et al. "Active-site zinc ligands and activated $H_2O$ of zinc enzymes," *Proc. Natl. Acad. Sci. USA* Jan. 1990;87(1):220-4.

Wetterholm, A. et al. "Recombinant mouse leukotriene $A_4$ hydrolase: a zinc metalloenzyme with dual enzymatic activities," *Biochim. Biophys. Acta* Oct. 25, 1991;1080(2):96-102.

Wetterholm, A. et al. "Leukotriene $A_4$ hydrolase: abrogation of the peptidase activity by mutation of glutamic acid-296," *Proc. Natl. Acad. Sci. USA* Oct. 1, 1992;89(19):9141-5.

Wetterholm, A. et al. "Potent and selective inhibitors of leukotriene $A_4$ hydrolase: effects on purified enzyme and human polymorphonuclear leukocytes," *J. Pharmacol. Exp. Ther.* Oct. 1995;275(1):31-7.

Yamaoka, K.A. et al. "Leukotriene $B_4$ enhances activation, proliferation, and differentiation of human B lymphocytes," *J. Immunol.* Sep. 15, 1989;143(6):1996-2000.

Yokomizo, T. et al. "A G-protein-coupled receptor for leukotriene $B_4$ that mediates chemotaxis," *Nature* Jun. 5, 1997;387(6633):620-4.

Yokomizo, T. et al. "A second leukotriene $B_4$ receptor, BLT2. A new therapeutic target in inflammation and immunological disorders," *J. Exp. Med.* Aug. 7, 2000;192(3):421-32.

Yuan, W. et al. "Novel tight-binding inhibitors of leukotriene $A_4$ hydrolase," *J. Am. Chem. Soc.* Apr. 1992;114:6552-53.

GenPept Acc. No. S65947; leukotriene-A4 hydrolase (EC 3.3.2.6) long isoform—human.

Marietta, Eric V. et al., "Transglutaminase Autoantibodies in Dermatitis Herpetiformis and Celiac Sprue," *Journal of Investigative Dermatology*, vol. 128:332-335 (2007).

Sárdy, Miklós et al., "Epidermal Transglutaminase (TGase 3) Is the Autoantigen of Dermatitis Herpetiformis," *J. Exp. Med.*, vol. 195(6):747-757 (2002).

* cited by examiner

94 —

67 —

43 —

30 —

Fig. 9 though the
amino acid sequence identity between guinea pig and human
TGc's is 82.8%, this test gave high sensitivity and specificity
above 90% (Ikura K et al., Biochemistry 1988; 27:2898-905;
Gentile V et al., J Biol Chem 1991; 266:478-83; Dieterich W et
DIAGNOSIS OF GLUTEN SENSITIVE ENTEROPATHY AND OTHER AUTOIMMUNOPATHIES

RELATED APPLICATIONS

This application is a 35 U.S.C. §371 filing of International Application Number PCT/EP00/06025, entitled "Diagnosis of Gluten Sensitive Enteropathy and Other Autoimmunopathies" filed on Jun. 28, 2000, which claims priority to European Patent application 99111975.1, filed Jun. 28, 1999. The contents of the aforementioned applications are hereby incorporated by reference.

TECHNICAL FIELD

The invention relates to the diagnosis of gluten sensitive enteropathy and other autoimmune diseases comprising the detection of antibodies against transglutaminases.

BACKGROUND ART

Gluten sensitive enteropathy (GSE) is a common chronic small bowel disorder of autoimmune origin occurring both in children and adults. It is evoked and maintained by wheat gluten which is also present in other cereals. The clinical appearance of GSE is typically coeliac disease (CD). In some individuals, however, it is associated with dermatitis herpetiformis (DH), a bullous, autoimmune skin disease characterised by granular IgA staining of the papillary dermis. Both of these forms of GSE have the same genetic background and have been associated with HLA class II antigens DQ2, and DR3, and the HLA-A1, -B8, -DR3 haplotype. In case of ingestion of gluten and the presence of genetic predisposition, a T-cell mediated autoimmune response develops in the small bowel first resulting in lymphocytic infiltration, later reduction followed by total atrophy of the villi leading to a disturbed resorption (Marsh M N et al., Bailliere Clin Gastr 1995.9:273-294). On a completely gluten-free diet, however, the pathological alterations entirely disappear and a normal morphology and function is restored.

The diagnosis of GSE is based on the characteristic histological changes (villous atrophy, intraepithelial lymphocytosis, crypt hyperplasia) seen in jejunal biopsies, followed by the regeneration of the mucosa after a gluten-free diet and relapse during subsequent gluten challenge. However, serological tests may be helpful in the diagnosis of GSE as they offer a less invasive and cheaper alternative. These detect IgA antibodies directed against endomysial antigen, reticulin, or gliadin. The IgA-class endomysial antibody (EMA) test is considered to be the serological method of choice, because of its higher sensitivity and specificity when compared to the IgA-class anti-reticulin antibody and the IgA-class anti-gliadin antibody tests. EMA is found in 60-70% of untreated patients with DH and in almost all untreated patients with CD. The EMA test is performed, however, on expensive oesophagus sections from endangered primates, is laborious and time consuming, and subjective in borderline cases.

Tissue transglutaminase (TGc, EC 2.3.2.13) was further identified as the predominant or sole endomysial autoantigen of CD (Dieterich W et al., Nature Medicine 1997, 3(7):797-801). An ELISA test for CD has been produced based upon the commercially available guinea pig TGc. Although the amino acid sequence identity between guinea pig and human TGc's is 82.8%, this test gave high sensitivity and specificity above 90% (Ikura K et al., Biochemistry 1988; 27:2898-905; Gentile V et al., J Biol Chem 1991; 266:478-83; Dieterich W et al., Gastroenterology 1998; 115:1317-21; Sulkanen S et al, Gastroenterology 1998; 115:1322-8).

OBJECT OF INVENTION

It was an object of the invention to provide an improved assay for gluten sensitive enteropathies and in particular an antibody binding assay which allows a differential diagnosis of autoimmune diseases of the GSE-type, autoimmune diseases associated with GSE and seemingly non-active, latent gluten sensitive enteropathies.

BRIEF DESCRIPTION OF INVENTION

This object has been achieved by providing a comparative protein binding assay based on recombinant human tissue transglutaminase and other transglutaminases for a differential diagnosis of gluten sensitive enteropathy (GSE), autoimmune diseases of the GSE-type, autoimmune diseases associated with GSE and a group of autoimmune diseases associated with IgA and IgG against transglutaminases. A preferred embodiment of the invention relates to a multiple protein binding assay comprising human tissue transglutaminase and other transglutaminases as binding partners. A more preferred embodiment of the invention relates to a protein binding assay comprising transglutaminases isolated or cloned from different tissues and species.

Another aspect of the invention relates to a method for diagnosis of autoimmune diseases of the GSE-type comprising a multiple protein binding assay on the basis of human TGc and other trans-glutaminases such as guinea pig TGc or other members of the transglutaminase protein family. Multiple or comparative protein binding assay means herewith that the diagnosis is done on basis of at least two, preferably three or more differing transglutaminase molecules as antigens.

The present invention provides a method for diagnosis of autoimmune diseases of the GSE-type of associated with gluten sensitive enteropathy comprising taking a sample and testing the sample for antibodies against tissue transglutaminase and at least one other transglutaminase. In a preferred embodiment, the autoimmune disease is dermatitis herpetiformis, morbus Duhring, or an autoimmune disease selected from Addison's disease, AI (AI—autoimmune) haemolytic anaemia, AI thrombocytopenic purpura, AI thyroid diseases, IDDM, alopecia, atrophic gastritis—pernicious anaemia, Crohn's disease, hypoadrenalism, hypogonadism, hyposplenism, cryoglobulinism, colitis ulcerosa, Goodpasture syndrome, gluten-induced ataxia, IgA nephropathy or IgA glomerulonephritis, myasthenia gravis, partial lipodystrophy, polymyositis, primary biliary cirrhosis, primary sclerosing cholangitis, progressive systemic sclerosis, oral aphthosis, recurrent pericarditis, relapsing polychondritis, rheumatoid arthritis, rheumatism, sarcoidosis, sensory neuropathy, seizures, Sjogren's syndrome, SLE, splenic atrophy, type I (insulin-dependent) diabetes mellitus, diabetes mellitus of other types, transaminitis, Wegener granulomatosis, ulcerative colitis, vasculitis (both systemic and cutaneous), and vitiligo. A further group of autoimmune diseases that can be diagnosed or distinguished in this way is associated with infertility, increased risk of abortion and/or reduced fetal growth.

The invention also provides a comparative protein binding assay for a differential diagnosis of autoimmune diseases comprising the detection of antibodies against transglutaminase, which protein binding assay comprises recombinant human tissue transglutaminase as antigen. In a preferred embodiment, the comparative protein binding assay comprises further a tissue-specific transglutaminase as antigen, preferably, a transglutaminase selected from FXIIIA, TGk, TGe, TGx, and so-called Band 4.2. The comparative protein binding assay may also contain any other transglutaminase as antigen, in particular, transglutaminase from different species. The skilled person will appreciate that a recombinant fusion protein or fragment thereof can also be used. The comparative protein binding assay is preferably an immunoassay selected from RIA, EIA/ELISA, LiA and FiA and most preferably a sandwich-immunoassay selected from IRMA, IEMA/EUA, ILMA (immunoluminescence assay) and IFMA (immunofluorescence assay).

Astonishingly, it has been found that despite the high amino acid sequence identity between human and guinea pig TGc, some of the tested patient sera not recognised by the guinea pig TGc ELISA had antibodies directed against epitopes of human TGc not conserved in the guinea pig enzyme. Our studies support that TGc is the autoantigen of EMA positive patients also with DH. Moreover, we discovered that there is a class of autoimmune diseases wherein transglutaminases plays a decisive role in the aetiology of the disease, which autoimmune diseases can be distinguished via the unique epitope pattern's of the various transglutaminases.

The discovery of TGc as the main autoantigen in GSE did not answer the question why only a proportion of patients with CD also show symptoms of DH and if, whether there is a difference in the antigenic repertoire in these diseases. It was unknown whether the granular IgA precipitates in the skin, of DH patients are directed against an antigen present in the skin or if they represent circulating immune complexes deposited in the papillary dermis. The IgA precipitates have so far not been extracted from skin and characterised. However, immunostaining for TGc does not give the same staining pattern as can be seen by direct immunofluorescence studies for IgA precipitates in the skin of DH patients. This suggests that the antigen against which the deposited IgA antibodies are directed might be different from the TGc. We now assume that these antibodies derive from cross-reactivity with another transglutaminase being present in the papillary dermis. Such a limited cross-reactivity could be a plausible explanation for the moderate penetrance of skin eruptions in patients with CD. It is also unclear why the pathological changes and clinical symptoms have a very limited localisation with only the small intestine and, in case of DH, the skin being affected, as TGc is present in almost every tissue of the human body. To address these questions, we expressed three other transglutaminases which can be found in the skin, the human TGk, TGe and TGx, in human embryonic kidney cells, to measure circulating IgA and IgG titres in patients with CD, DH and other autoimmune diseases.

BRIEF DESCRIPTION OF DRAWINGS

The invention wilt now be described in detail with reference to the accompanying drawings and representations. No limitation of the invention whatsoever shall be construed from the description of the representative examples.

FIG. 9 SDS-PAGE analysis of TGe after purification. Positions of molecular mass standards (kDa) are indicated on the left.

DETAILED DESCRIPTION OF INVENTION

Figure 1:
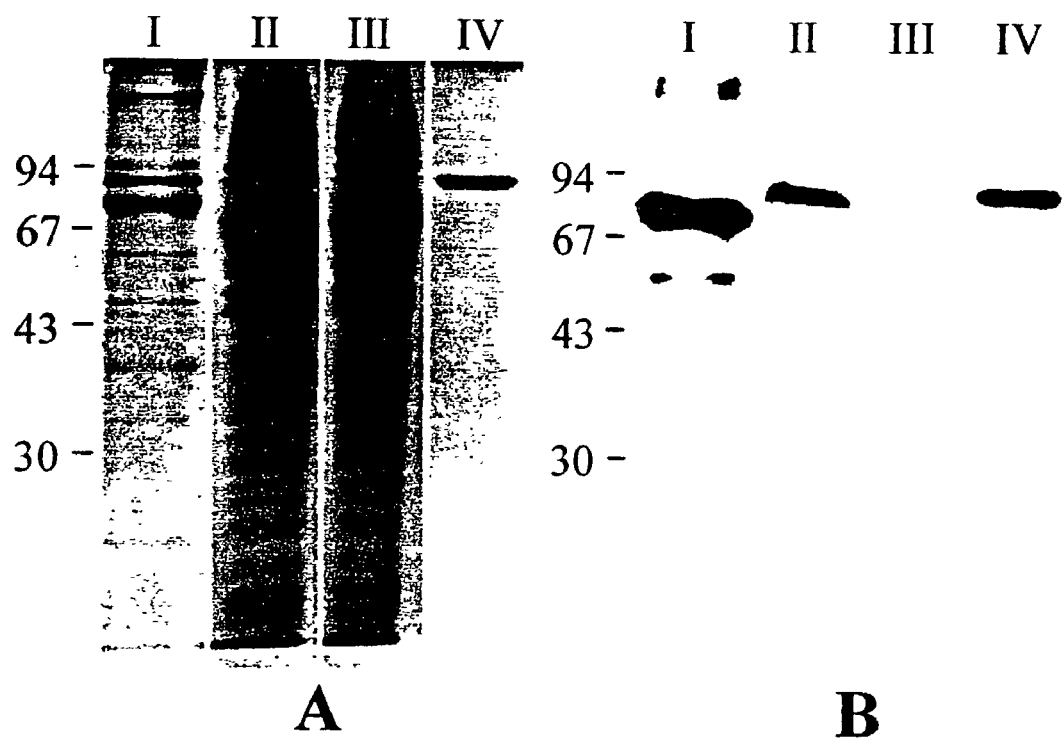
FIG. 1 SDS-PAGE (A) and immunoblot (B) analysis of TGc. The immunoblot was performed using monoclonal antibodies against TGc. Positions of molecular mass standards (kDa) are indicated on the left Lane I, guinea pig TGc; lane II, lysate of cells producing recombinant human TGc before purification; lane III, flow through; lane IV, eluted TGc from the column.

The inventors expressed human TGc and other transglutaminases by recombinant DNA methods and set up various ELISAs based on the purified proteins for detecting IgA anti-TG antibodies. The results of these assays were compared to those from the ELISA with the guinea pig TGc and the EMA test on monkey oesophagus.

METHODS AND MATERIALS

SDS-PAGE and Immunoblotting

SDS-PAGE (Sodium dodecyl sulphate polyacrylamide gel electrophoresis) was performed according to the method of Laemmli (Laemmli, Nature 1970; 227:680-5) using a 12% polyacrylamide separating gel with a 5% polyacrylamide stacking gel. Samples were reduced by addition of 2% (v/v) 2-mercaptoethanol. Proteins were detected either by staining with Coomassie Brilliant Blue R (Serva) or by immunoblotting after electrophoretic transfer to a nitro-cellulose membrane (Protran, Schleicher & Schuell) according to the method of Towbin and co-workers (Towbin H et al, Proc Natl Acad Sci USA, 1979; 76:4350-4). After protein transfer, the membranes were stained with Ponceau S (Serva), then blocked with 50 mM Tris, 150 mM NaCl, pH 7.4 (TBS) containing 5% non-fat milk powder for 75 min. at room temperature. The blocked membrane was then incubated with the specific antibody.

Human TGc was detected with mouse monoclonal antibodies against TGc (specific for TGc, but cross-reacting both with human and guinea pig TGc, Neomarkers, Ab-3, CUB7402+TG100) diluted 1:2000 in TBS containing 5% non-fat milk powder and 0.05% Tween™ 20 (Sigma) for 1.5 hours at room temperature. For detection of bound mouse antibodies, membranes were incubated with horse radish peroxidase labelled rabbit antibodies directed against mouse immunoglobulins (Dako), diluted 1:2000 in TBS/Tween containing 5% non-fat milk powder for 1 hour at room temperature. Bound secondary antibodies were detected by autoradiography using the enhanced chemiluminescence system (ECL Kit, Amersham). Guinea pig TGc (Sigma) was used each time as a positive control.

Recombinantly expressed TGs were detected by using rabbit-polyclonal-antibodies against the Strep II tag (Institut für Bioanalytik) diluted 1:5000 in TBS containing 1% non-fat milk powder and 0.05% Tween 20 (Sigma) for 1 h at room temperature. For detection of bound rabbit antibodies, membranes were incubated with horseradish-peroxidase-labelled swine antibodies against rabbit immunoglobulins (Dako), diluted 1:3000 in TBS/Tween containing 1% non-fat milk powder for 1 hour at room temperature. Bound secondary antibodies were detected by luminescence after incubation 5 min in 100 mM Tris/HCl, pH 8.3, containing 0.2 mM p-coumaric acid (Sigma), 2.65 mM H2O2 (Sigma) and 1.25 mM 3-aminophthalhydrazide (Fluka). Human TGc expressed as a fusion protein with a C-terminal Strep II tag was used as a positive control.

Reverse Transcription and Polymerase Chain Reaction.

Reverse transcription was performed using AMV reverse transcriptase (Oncor Appligene) and PCR using Pfx Taq polymerase (Life Technologies) following the protocols provided by the manufacturers.

Recombinant Expression of Human TGc.

The episomal eukaryotic expression vector pCEP-Pu/BM40SP, produced from pCEP4 (Invitrogen) (Kohfeldt E et al, FEBS Lett 1997; 414:557-61), was modified to introduce a sequence encoding the Strep II tag (IBA, Germany) and a stop codon into the multiple cloning site. The primers 5'-GGCCGCATGGAGCCATCCACAATTCGAAAAGTA (SEQ ID NO: 1) and 5'-GGCCTACTTTTCGAATTGTGGATGGCTCCATGC (SEQ ID NO: 2) were annealed together and introduced into the Not I site thus constructing a vector (pCEP-Pu/BM40SP/C-Strep) producing a carboxyterminal Strep II fusion protein suitable for streptavidin affinity purification by a StrepTactin™ (IBA, Germany) affinity column as described before by Schmidt TGM et al (J Mol Biol 1996; 255:753-66). The full-length human TGc cDNA (GeneBank accession number M55153, cloned in pSP73) was amplified by polymerase chain reaction (PCR) using the 5'-primer 5'-ATTAAGCTTGCCGCCACCATGGCCGAGGAGCTGGTC (SEQ ID NO: 3), and the 3'-primer 5'-TAAGCGGCCGCGGGGCCAATGATGACATTC (SEQ ID NO: 4). The 5'-primer introduced a new Hind III restriction site and a Kozak's translation initiation sequence, the 3'-primer inserted a new Not I restriction site and removed the stop codon. The Hind III/Not I restriction enzyme digested PCR product was purified and inserted at the same restriction sites of the pCEP-Pu/BM40SP/C-Strep, in order to obtain the final expression vector pCEP-Pu/TGc/C-Strep. The correct insertion and sequence of the full construct was verified by cycle sequencing using the ABI Prism Big Dye Terminator Cycle Sequencing Ready Reaction Kit and the products were resolved on an ABI Prism 377 Automated Sequencer (Perkin-Elmer/Applied Biosystems).

Human embryonic kidney cells (293-EBNA, Invitrogen) were transfected with pCEP-Pu/TGc/C-Strep and harvested in cell culture in Dulbecco's MEM NUT MIX F-12 (Life Technologies) medium containing 10% foetal bovine serum (Life Technologies), 1% L-glutamine (Life Technologies), 200 IU/ml penicillin (Life Technologies), and 200 µg/ml streptomycin (Life Technologies). Cells were selected with 0.5 µg/ml puromycin. After removing the medium and washing with cold (4° C.) 0.25 M sucrose, the cells were lysed mechanically in cold 0.25 M sucrose. The lysate was cleared of particulate material by centrifugation at 27,200 g for 30 min at 4° C., followed by ultracentrifugation of the supernatant at 210,000 g for 60 min at 4° C. After filtering with cheesecloth and adding 1 mM phenylmethanesulfonyl fluoride (PMSF, Fluke) as proteinase inhibitor, 12 ml of the supernatant was passed over a StrepTactin affinity column of 3 cm$^3$ volume-equilibrated with sterile and filtered 50 mM Tris/HCl, pH 7.5, containing 1 mM ethylenediamine tetraacetate (EDTA), at 4° C., and at a flow rate of 0.4 ml/cm$^2$/min. After extensive washing with equilibration buffer containing 1 mM PMSF, at a flow rate of 0.9 ml/cm$^2$/min, the protein was eluted with equilibration buffer containing 1 mM PMSF and 2.5 mM desthiobiotin (Sigma), at a flow rate of 0.4 ml/cm$^2$/min. 2 ml fractions were collected. The purification was controlled by Coomassie-stained SDS-PAGE and Western Blotting with monoclonal antibodies against TGc as described above. The protein concentration was estimated by SDS-PAGE, and measured using the bicinchoninic acid (BCA) protein assay reagent (Pierce) following the protocol provided by the supplier, with bovine serum albumin as a standard.

Production of cDNAs from Various Transglutaminases.

Total RNA from human keratinocytes was reversely transcribed with primers specific for the TGe and TGk proenzymes, and PCR used to obtain cDNAs. Full-length human TGx cDNA (GeneBank accession number AF035960) was cloned in pSP73.

Production of an Expression Construct for the Expression of TGe.

An episomal expression construct was built allowing the production of a C-terminal Strep II fusion protein suitable for streptavidin affinity purification by a StrepTactin™ (Institut für Bioanalytik, Germany) affinity column (Schmidt TGM et al., J Mol Biol 1996; 255:753-66.). The TGe proenzyme cDNA was amplified by PCR using the 5'-primer 5'-ATTAAGCTTGCCGCCACCATGGCTGCTCTAGGAGTC (SEQ ID NO: 5), and the 3'-primer 5'-ATTGCGGCCGCT- TCGGCTACATCGATGGACAAC (SEQ ID NO: 6). The 5'-primer introduced a new Hind III restriction site and a Kozak's translation initiation sequence, while the 3'-primer inserted a new Not I restriction site and removed the stop codon. The Hind III/Not I restriction enzyme digested PCR product was purified and inserted at the same restriction sites of the episomal eukaryotic expression vector pCEP-Pu/BM40SP/C-Strep, produced from pCEP4 (Invitrogen), in order to obtain the final expression vector pCEP-Pu/TGe/C-Strep.

Construction of the Expression Vector pCEP4/N-Strep.

The eukaryotic episomal expression vector pCEP4 (Invitrogen) was modified to introduce a sequence encoding a Kozak's translation initiation sequence and the Strep II tag into the multiple cloning site. The primers 5'-CTAGTTGC-CGCCACCATGGCTTGGAGCCATCCACAATTC-GAAAAGG (SEQ ID NO: 7) and 5'-CTAGCGCCTTTTC-GAATTGTGGATGGCTCCAAGCCATGGTGGCGGCAA (SEQ ID NO: 8) were annealed together and introduced into the Nhe I site thus constructing a vector (pCEP4/N-Strep) producing an N-terminal Strep II fusion protein.

Production of Expression Constructs for the Expression of TGx.

Two episomal expression constructs were built allowing the production of both a C-terminal and an N-terminal Strep H fusion protein. For the construct with C-terminal Strep H tag, the TGx cDNA was amplified by polymerase chain reaction (PCR) using the 5'-primer 5'-ATTGCGGCCGCCATG-GCCCAAGGGCTAGAAG (SEQ ID NO: 9), and the 3'-primer 5'-TAAGCGGCCGCTAATGCAAAGTCTACAT-AAAC (SEQ ID NO: 10). The 5'-primer introduced a new Not I restriction site and a Kozak's translation initiation sequence, while the 3'-primer inserted a new Not I restriction site and removed the stop codon. The Not I restriction enzyme digested PCR product was purified and inserted at the same restriction sites of pCEP4 in order to obtain the final expression vector pCEP4/TGx/C-Strep. For the construct with N-terminal Strep II tag, the TGx cDNA was amplified by polymerase chain reaction (PCR) using the 5'-primer 5'-AT-TGCTAGCCCAAGGGCTAGAAGTGG (SEQ ID NO: 11), and the 3'-primer 5'-TAAGCGGCCGCTTATAATG-CAAAGTCTACATAAAC (SEQ ID NO: 12). The 5'-primer introduced a new Nhe I restriction site and removed the first methionine, the 3'-primer inserted a new Not I restriction site directly after the stop codon. After digesting with the restriction enzymes Nhe I and Not I the PCR product was purified and inserted at the same restriction sites of pCEP4 in order to obtain the final expression vector pCEP4/N-Strep/TGx.

Construction of Expression Constructs for the Expression of TGk.

Two episomal expression constructs were built allowing the production of both a C-terminal and an N-terminal Strep II fusion protein. For the construct with C-terminal Strep II tag, the TGk proenzyme cDNA was amplified by polymerase chain reaction (PCR) using the 5'-primer 5'-ATTAAGCT-TGCCGCCACCATGATGGATGGGCCACGTTCC (SEQ ID NO: 13), and the 3'-primer 5'-ATTGCGGCCGCAGCTC-CACCTCGAGATGCCATAGG (SEQ ID NO: 14). The 5'-primer introduced a new Hind III restriction site and a Kozak's translation initiation sequence, while the 3'-primer inserted a new Not I restriction site and removed the stop codon. The Hind III/Not I restriction enzyme digested PCR product was purified and inserted at the same restriction sites of pCEP-Pu/BM40SP/C-Strep, in order to obtain the final expression vector pCEP-PuTGk/C-Strep. For the construct with N-terminal Strep II tag, the TGk proenzyme cDNA was amplified by polymerase chain reaction (PCR) using the 5'-primer 5'-ATTGCTAGCAGATGGGCCACGTTC-CGATG (SEQ ID NO: 15), and the 3'-primer 5'-ATTGGATC-CTAAGCTCCACCTCGAGATGC (SEQ ID NO: 16). The 5'-primer introduced a new Nhe I restriction site and removed the first two methionines, while the 3'-primer inserted a new Not I restriction site directly after the stop codon. After digesting with the restriction enzymes Nhe I and Not I the PCR product was purified and inserted at the same restriction sites of pCEP4, in order to obtain the final expression vector pCEP4/N-Strep/TGk. The correct insertion and sequence of the full constructs was verified by cycle sequencing as described above.

Recombinant Expression of the Human TGe, TGx, and TGk.

Human embryonic kidney cells (293-EBNA, Invitrogen) were transfected and harvested in cell culture in Dulbecco's MEM NUT MIX F-12 (Life Technologies) medium containing 10% foetal bovine serum (Life Technologies), 1% L-glutamine (Life Technologies), 200 IU/ml penicillin (Life Technologies), and 200 µg/ml streptomycin (Life Technologies). Cells transfected with pCEP-Pu constructs were selected with 0.5 µg/ml puromycin (Sigma), those with pCEP4 with 333 µg/ml (335 U/ml) hygromycin B (Calbiochem). After removing the medium and washing with cold (4° C.) 0.25 M sucrose, the cells were lysed mechanically in cold 0.25 M sucrose. The lysate was cleared of particulate material by centrifugation at 27,200 g for 30 min at 4° C., followed by ultracentrifugation of the supernatant at 210,000 g for 60 min at 4° C. After filtering with cheesecloth and adding 1 mM PMSF (Fluka) as proteinase inhibitor, 12-72 ml of the supernatant was passed over a StrepTactin™ affinity column of 3 $cm^3$ volume equilibrated with sterile and filtered 100 mM Tris/HCl, pH 7.5, containing 1 mM EDTA, at 4° C., and at a flow rate of 0.4 ml/$cm^2$/min. After extensive washing with equilibration buffer containing 1 mM PMSF, at a flow rate of 0.9 ml/$cm^2$/min, the protein was eluted with equilibration buffer containing 1 mM PMSF and 2.5 mM desthiobiotin (Sigma), at a flow rate of 0.4 ml/$cm^2$/min. 2 ml fractions were collected. The purification was controlled by SDS-PAGE and immunoblotting with monoclonal antibodies against the Strep tag as described above. The protein concentration was estimated by SDS-PAGE, and measured using the bicinchoninic acid (BCA) protein assay reagent (Pierce) following the protocol provided by the supplier, with bovine serum albumin as a standard.

Transglutaminase Activity Assay

TGc and TGe activity was measured by incorporation of [1,4-$^3$H]putrescine (Amersham) 30 min. at 37° C. as described before (Aeschlimann D et al., J Biol Chem 1991; 266:15308-17), with the only difference that the buffer contained 7.5 mM dithiothreitol in order to reduce any oxidised sulfhydryl groups important for catalytic activity. The TGe was activated by partial proteolytic digestion preincubating it 20 min at 37° C. together with either 45.4 µg/ml (0.5 U/ml) proteinase K (Sigma), or 45.4 µg/ml (55.4 U/ml) trypsin 1:250 (Sigma), or 1.18 mg/ml (1 U/ml) dispase (Life Technologies).

Mass Spectrometry

Mass spectrometry of TGc and TGe was performed by matrix-assisted laser desorption method using a Bruker Reflex III instrument equipped with a high mass detector for linear detection. Sinapinic acid was used as matrix, and external calibration was carried out using singly, doubly and triply charged molecular ions of protein A.

Sera and Patients

In the first study, the patients had been examined at the Gastroenterological Departments of Internal Medicine or Paediatrics and the Department of Dermato-Venereology of the Semmelweis University. The CD diagnosis was confirmed by jejunal biopsy while DH was proven by skin biopsy. Serum samples were taken from 71 patients with GSE (33 with DH, and 38 with CD), 26 with non-CD gastrointestinal diseases (such as M. Crohn, food hypersensitivity, food intolerance, intestinal infection, reflux oesophagitis, non-CD diarrhoea, alimentary dystrophy), and 27 with other diagnoses like autoimmune diseases (systemic lupus erythematosus, diabetes mellitus type I), different skin disorders (pemphigus foliaceus, ichthyosis, urticaria), cholelithiasis, hepatosplenomegalia, nanosomia, and healthy controls. The mean age and sex of patients' groups are presented in Table 1.

TABLE 1

Age (at the time of blood sampling, in years) and sex of patients

|  | CD | DH | GI | Others | Altogether |
|---|---|---|---|---|---|
| Mean age | 18.5 | 30.2 | 17.4 | 17.0 | 20.8 |
| Min. age | 3 | 6 | 1 | 12 | 1 |
| Max. age | 51 | 74 | 78 | 53 | 78 |
| Male/female | 20/18 | 13/20 | 14/12 | 14/13 | 61/63 |

To obtain data on the sensitivity of TGc ELISA, we included in the current study sera from 16 treated patients (patients on a gluten-free diet).

In the supplementary study on GSE associated autoimmune diseases the sera were obtained from the Gastroenterological Department of Internal Medicine or Paediatrics and the Department of Dermato-Venereology of the Semmelweis University, the Departments of the Internal Medicine I-IV of the Medical Faculty of the University Cologne, and from the Laboratory for Autoimmune Diseases of the Wieslab Co. Sweden. Serum samples were taken from patients with the following autoimmune diagnoses (number of patients in parentheses): GSE (141; from which 73 DH including 18 on a gluten-free diet, and 68 CD including 27 on a gluten-free diet), Crohn disease (31), bullous pemphigoid (44), pemphigus vulgaris (57), colitis ulcerosa (21), Goodpasture syndrome (20), Wegener granulomatosis (20), rheumatoid arthritis (44), SLE (25), progressive systemic sclerosis (7). Sera from patients with psoriatic arthritis (5) and hepatitis C (39) were also studied as these diseases may have an autoimmune component.

All serum samples were stored at −78 C until assayed. Among the control sera (48) some were from healthy individuals (21) and some from patients suffering from disease that does clearly not have an autoimmune component (27). All serum samples were stored at −78 C until assayed.

EMA Test.

Serum IgA antibodies were measured by an indirect immunofluorescence method (Collin P et al, Scand J Gastroenterol 1992; 27:367-71). All serum samples were diluted 1:5 in phosphate-buffered saline (PBS, pH: 7.4). 10 µm cryostat tissue slides of the aboral part of monkey (Cercopithecinae family) oesophagus were used as antigen. Bound IgA was detected by a-chain specific, fluorescein isothiocyanate-conjugated rabbit anti-human IgA antibodies (1:40 in PBS; Dako). All sera used in the first study were indisputably negative or positive for IgA EMA. In the supplementary study, no EMA test was performed.

ELISA.

The ELISA method was similar to the calcium-activated test described previously (Dieterich W et al, Gastroenterology 1998; 115:1317-21; Sulkanen S et al., Gastroenterology 1998; 115:1322-8). Briefly: 96 well microtiter plates (Nunc MaxiSorp) were coated by 1 µg guinea pig TGc (Sigma) or human TGe or TGc per well in 100 µl of 50 mM Tris/HCl, pH 7.5, containing 5 mM $CaCl_2$ per well at 4° C. overnight (at least 9 hours). No blocking was used. After each step the wells were washed by 50 mM Tris/HCl containing 10 mM EDTA and 0.1% Tween 20 (TET). Sera were diluted to various concentrations with TET, or preincubated in 50 mM Tris/HCl containing 0.1% Tween 20 and various concentrations of TGc or TGe or guinea pig TG, and incubated on the plates for 1.5 hours at room temperature. Bound IgA was detected by peroxidase-conjugated anti-human IgA antibody (Dako), diluted 1:4000 in TET and incubated for 1 hour at room temperature. The colour was developed by 100 µl of 60 µg/ml 3,3',5,5'-tetramethylbenzidine substrate in 100 mM sodium acetate, pH 6.0, containing 0.015% $H_2O_2$ for 5 minutes at room temperature. The reaction was stopped by adding 100 µl of 20% $H_2SO_4$. The absorbance was read in an ELISA reader at 450 nm.

The amount of protein and the serum concentrations used in the test were optimised. All serum samples were examined in triplicates, and triplicates of a negative and a positive reference serum, as well as a buffer blank were included in each plate. The antibody concentrations were expressed in arbitrary units (AU), i.e. as percentages of the positive reference serum.

In order to get data about the effects of calcium-activation, an experiment coating with human TGc without $CaCl_2$ in the coating buffer was also performed.

Inhibition ELISA.

Serum IgA levels against TGe were compared with those against TGc. Four sera from patients with CD or DH were studied which had previously shown to contain slightly (1 serum), moderately (1 serum) or highly (2 sera) elevated serum IgA antibody titers against TGc. Blocking experiments were carried out by preincubating the sera at a serial dilution from 1:250 to 1:32000 in 50 mM Tris/HCl containing 0.1% Tween 20 and 1 µg of either TGe or TGc 60 min at room temperature. A serum dilution was chosen at which the greatest difference was detected between the antibody titers of the sera with and without preincubation. In the following inhibition experiment the four sera were preincubated at this dilution in 50 mM Tris/HCl containing 0.1% Tween 20 with a serial dilution ranging from 0-4 µg of either TGc or TGe 60 min at room temperature.

Statistics

Optical densities (and thus titres given in AU values) did not show Gaussian distribution, thus for statistical description of titers from the different patient groups, we present medians with their 95% confidence intervals (95% CI) (Gardner M J & Altman DG, eds. Statistics with confidence-confidence intervals and statistical guidelines. London: British Medical Journal, 1989:28 pp.) and for comparison Mann-Whitney's non-parametric, unpaired, two-tailed test was used (Werner J. Biomathematik und Medizinische Statistik, $2^{nd}$ ed. München-Wien-Baltimore: Urban & Schwarzenberg, 1992: 53 pp.). For describing correlation of titers, Spearman's correlation coefficient with its 95% CI and correlation analysis for unpaired data of non-normal distribution was used (Gardner and Altman, 1989; Werner, 1992).

For comparison of titres in the calcium-activated and inactivated human TGc ELISA, Wilcoxon's two-tailed signed rank test was performed (Werner, 1992). For describing and comparing of the two ELISA systems, the receiver operating characteristic (ROC) curves and the areas under the ROC curves (AUC) with their 95% CI are presented. For calculating confidence intervals of AUC, beside the most often used method also a bootstrap technique, the bias-corrected and accelerated ($BC_a$) confidence interval method was applied, as it is more appropriate in describing confidence intervals of AUC which are very close to the maximum (1.0) (DeLong E R et al. Biometrics 1988; 44:837-45; Mossman D., Med Decis Making 1995; 15:358-66; Hellmich M. Receiver operating characteristic (ROC) Kurven und Flächen darunter. [PhD thesis] 1996. http://www.medizin.-uni-koeln.de/kai/imsie/homepages/Martin.Hellmich/dr.html (accessed June 1999).

EXAMPLE

Recombinant Human TGc

The human TGc was expressed in the 293-EBNA human embryonic kidney cell line as a fusion protein with the Strep II tag. The protein could be purified in a single step by affinity binding to a StrepTactin column, on washing with desthiobiotin the protein eluted as a single band with an estimated molecular weight of 89 kDa (FIG. 1A) when visualised by Coomassie-stained SDS-PAGE. Western blot analysis showed that the band reacted with monoclonal anti-TGc antibodies (FIG. 1B). The column bound almost all the tagged protein with no immunoreactivity appearing in the flow through (FIG. 1B). The yield from the lysate of a confluent cell monolayer in a cell culture dish of 13 cm diameter was approximately 200 μg. The molecular mass calculated from the sequence of the human TGc is 77.3 kDa and the calculated molecular mass of the fusion protein (TGc having a carboxyterminal tag of 10 amino acids) is 78.4 kDa. Mass spectrometry of the fusion protein gave a molecular mass of 78.3 kDa. In cell lysates, the activity of the expressed human TGc was 4.7 times higher than the background activity of transglutaminases present in untransfected 293-EBNA cells. The freshly purified human TGc showed similar or higher activity than the guinea pig TGc from Sigma.

Performance of the Human TGc ELISA.

The optimal coating concentration of human TGc was 1 μg per well. Using highly positive sera from four patients for calibration, a log-linear curve was seen between dilutions of 1:250 and 1:32000. Four negative sera showed some signal at lower dilutions (>1:500). Some positive sera showed a signal plateau at dilutions of 1:250 or less. The ratio between the mean OD values of positive and negative results at the dilution of 1:125 was 1:6, while at greater dilutions more than 1:10. Hence in the assay a serum dilution of 1:250 was used. One positive and one negative reference serum sample was included in each assay to control the test performance. The positive serum was used as "standard", and the optical density results were given as arbitrary units (AU) calculated as a percentage of the standard serum. The mean intra- and interassay coefficients of variation for the standard serum were 1.3% and 13.7%, respectively. The mean intra- and interassay coefficients of variation for human TGc ELISA were 3.2% (n=124) and 9.2% (n=15), respectively.

Figure 2:
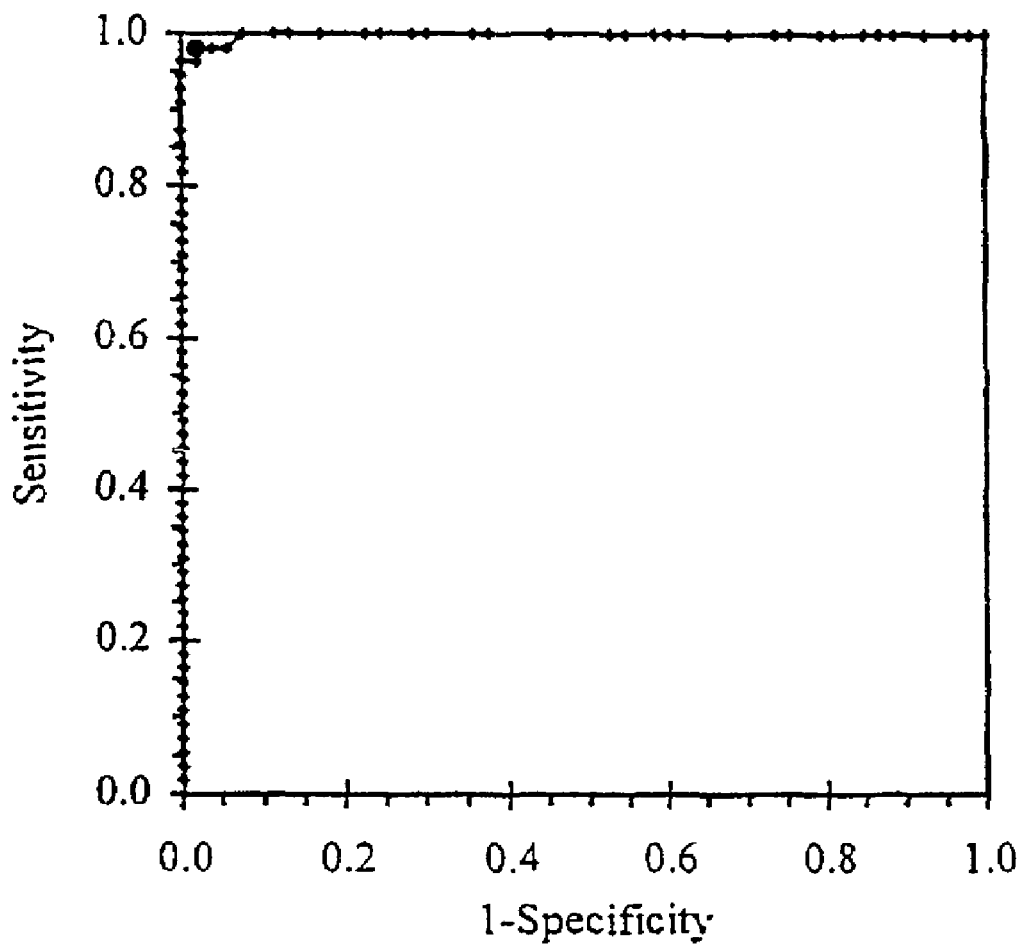
FIG. 2 Receiver operating characteristic curve (ROC) for the human TGc ELISA showing the point of greatest efficiency of the test, upon which the cut-off level was chosen.

The median antibody concentrations for the patients with untreated GSE (CD or DH) was 61.4 AU (n=55.95% CI: 45.1-78.5), for controls 12 AU (n=53.95% CI: 10.8-13), the difference was significant (p<0.0001). For treated patients, the median of antibody concentrations was 48.1 AU (n=16.95% CI: 20.8-85.6), for controls with gastrointestinal diseases 12.1 AU (n=26.95% CI: 9.8-14.7), for healthy individuals and controls with other diagnoses 12 AU (n=27.95% CI: 10.7-13.0), respectively. The area under the ROC curve was 0.999 (95% CI: 0.996-1.001; 95% CI with $BC_a$ method: 0.990-1.0) (FIG. 2).

Figure 3:
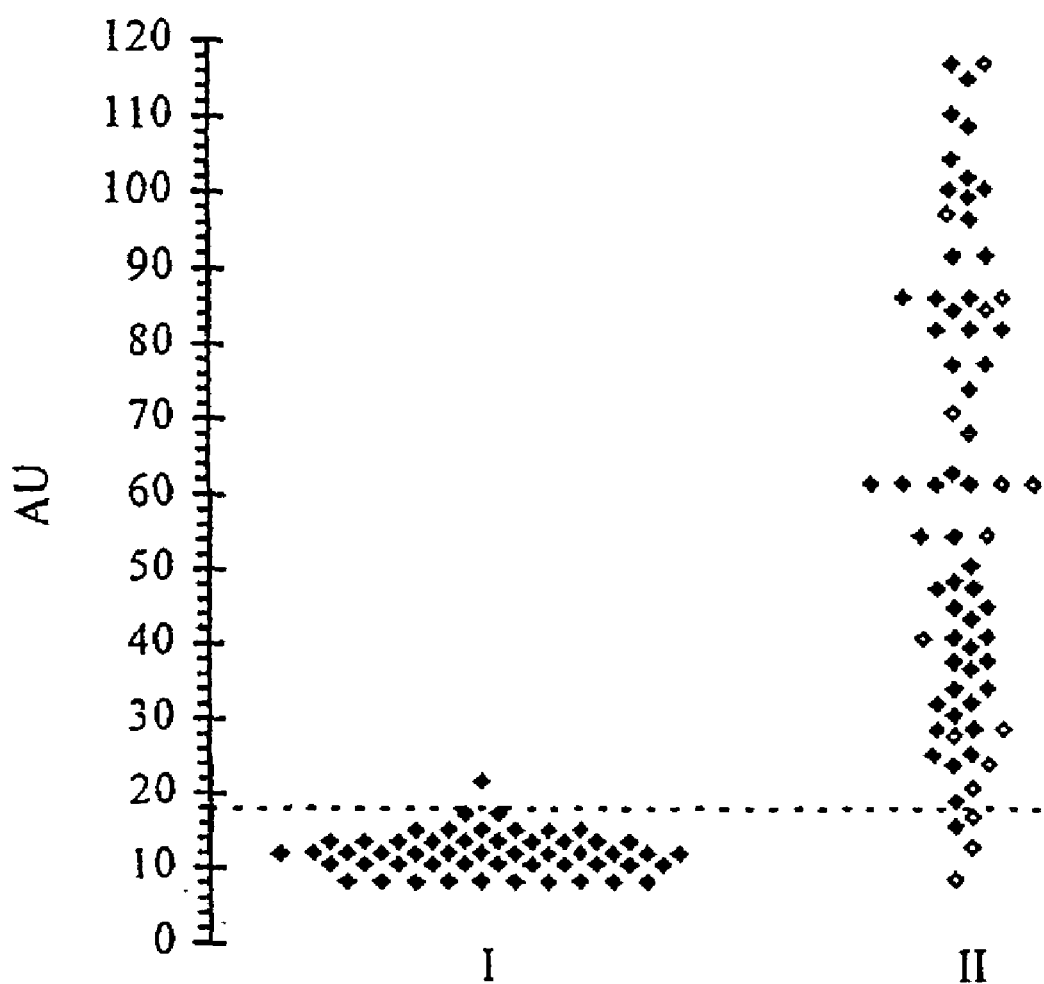
FIG. 3 Serum anti-TGc antibody concentrations in the human TGc ELISA system in the controls (I) and in the patients having CD or DH (II). Treated CD or DH patients are indicated by empty squares. The chosen arbitrary cut-off level for positivity (broken line) is drawn at the AU of 18.

A cut-off value of 18 AU was chosen, and sera with antibody concentrations equal or higher than 18 AU were labelled as human TGc ELISA positive. This cut-off value gave a specificity and a sensitivity of 98.1% (95% CI: 95.7-100%) and 98.2% (95% CI: 95.9-100%), respectively (treated patients are excluded). The coincidence of the human TGc assay with the clinical diagnosis (excluding treated patients) was 106/108 (98.1%), giving one false positive and one false negative result (FIG. 3).

Recombinant Human TGe

Figure 9:
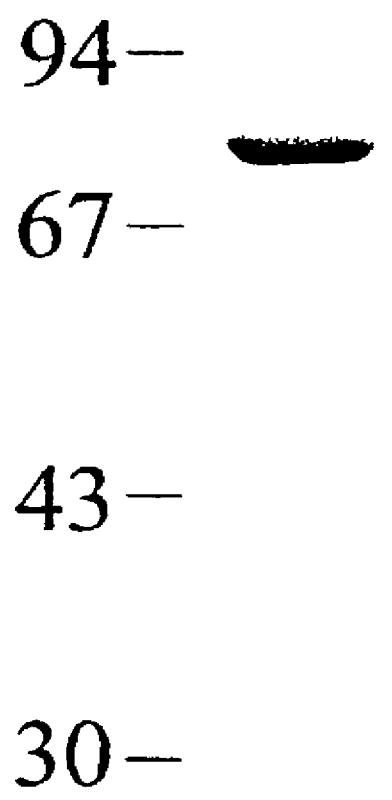
Figure 10:
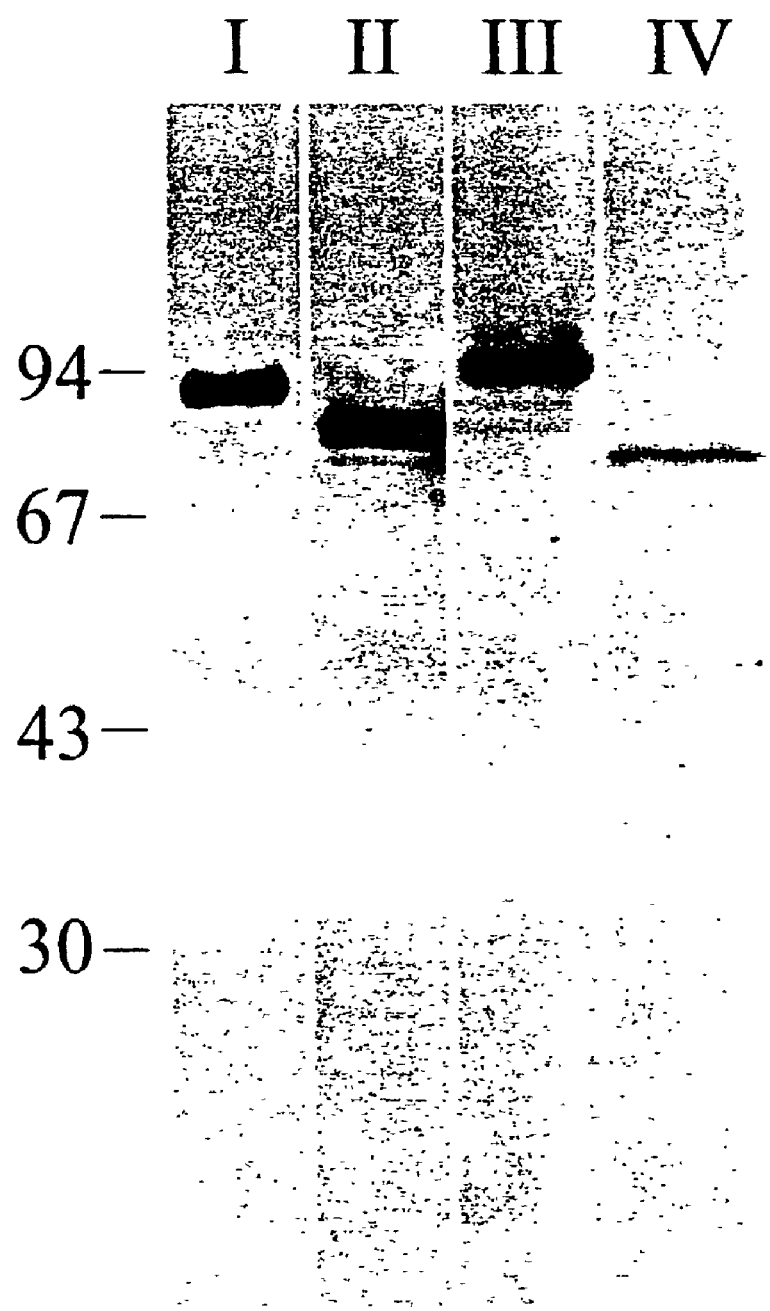
FIG. 10 Immunoblot analysis of the human TGs using polyclonal rabbit antibodies against the Strep II tag. Positions of molecular mass standards (kDa) are indicated on the left. Lane I, TGc; lane II, TGe; lane III, TGk; lane IV, TGx.

The human TGe was expressed in the 293-EBNA human embryonic kidney cell line as a fusion proenzyme with the Strep II tag. The protein could be purified in a single step by affinity binding to a StrepTactin™ column. After elution with desthiobiotin the protein gave a single 80 kDa band in SDS-PAGE (FIG. 9), which reacted with monoclonal antibodies against the Strep II tag (FIG. 10, lane II). The column bound almost all the tagged TGe with no immunoreactivity appearing in the flow through. The yield from the lysate of a confluent cell monolayer in a cell culture dish of 13 cm diameter was approximately 200 μg. The molecular mass calculated from the sequence of the human TGe proenzyme is 76826 Da, and the calculated molecular mass of the fusion protein (TGe proenzyme having a carboxyterminal tag of 10 amino acids) is 78011 Da. Mass spectrometry of the fusion protein gave a molecular mass of 77765 Da. In cell lysates, the activity of the expressed human TGe was 2.5 times higher than the background activity of transglutaminases present in untransfected 293-EBNA cells. The freshly purified human TGe proenzyme showed 1:40-1:80 of the activity of TGc and when activated with different proteases (proteinase K, trypsin or dispase) similar or higher activity than the TGc.

Performance of Human TGe ELISA.

Figure 11:
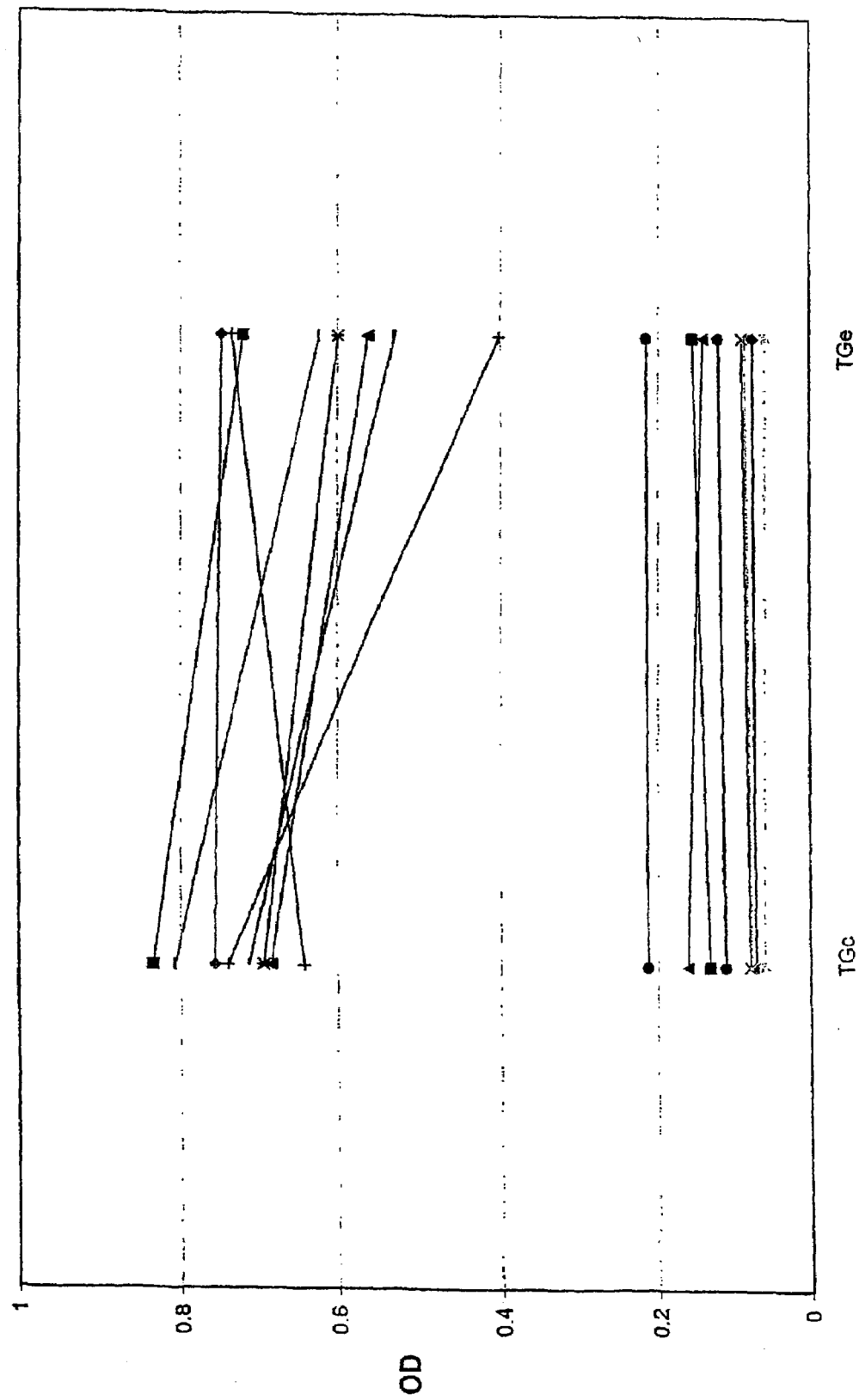
FIG. 11 Binding of IgA in GSE patient sera to human TGc or TGe in ELISA. Sera reacting with the TGc showing-values below 0.4 gave similar results with the TGe, but sera with elevated IgA antibody titres against TGc in the most cases showed lower antibody titres against TGe.

GSE sera showing elevated IgA antibody levels against the human TGc also showed elevated IgA titres against the human TGe, whereas sera not reacting with the human TGc did not react with the human TGe (FIG. 11). The antibody titres for TGe were in most cases lower than for TGc (FIG. 11).

Inhibition ELISA.

Figure 12:
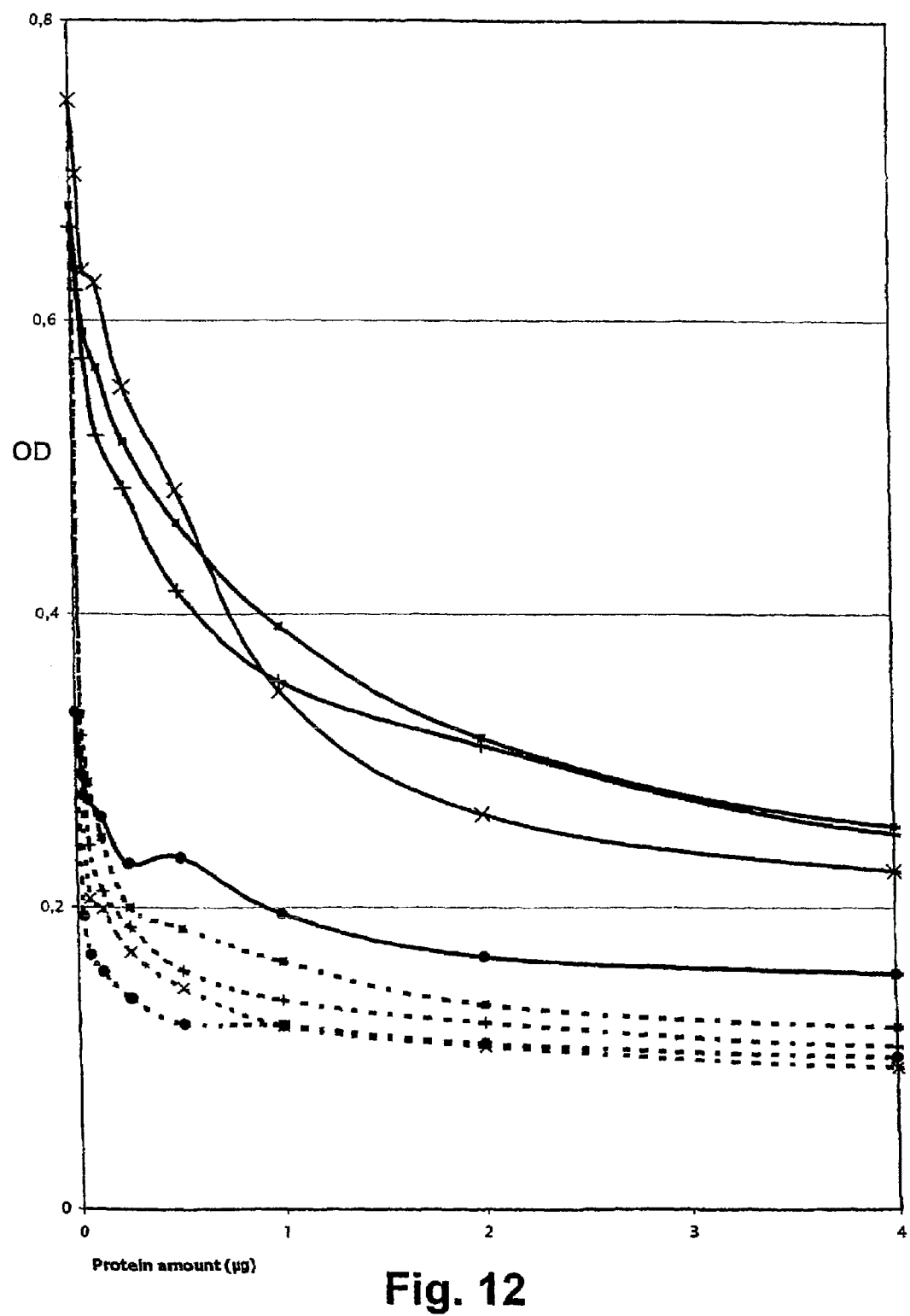
FIG. 12 Inhibition of binding of IgA in four GSE patient sera to solid phase human TGc by preincubation with increasing amounts of human TGc (dotted line) or TGe (continuous line). Both the TGc and the TGe showed an inhibitory effect, but the TGc was more effective than the TGe.

Preincubation of GSE sera with human TGc or TGe inhibited the IgA reactivity in an ELISA plate coated with human TGc (FIG. 12). The results shown support that serum IgA antibodies from patients with CD and DH react with both the human TGc and the TGe, although the titres to TGe is lower. Both TGc and TGe can inhibit the reaction of serum IgA antibodies with TGc. At least a part of the serum antibodies from patients with CD and DH is directed against epitopes which are shared by the two transglutaminases.

Performance of the Guinea Pig TGc ELISA.

The optimal coating concentration of guinea pig TGc was 1 μg per well and the optimal serum dilution 1:250, as with the human TGc ELISA. Each assay was performed parallel to the human TGc assay at the same time, and the same serum samples and serum dilutions were used. The mean intra- and interassay coefficients of variation of the standard serum were 2.2% and 9.0%, respectively. The intra- and interassay coefficients of variation for guinea pig ELISA were 2.8% (n=124) and 12.8% (n=15), respectively.

Figure 4:
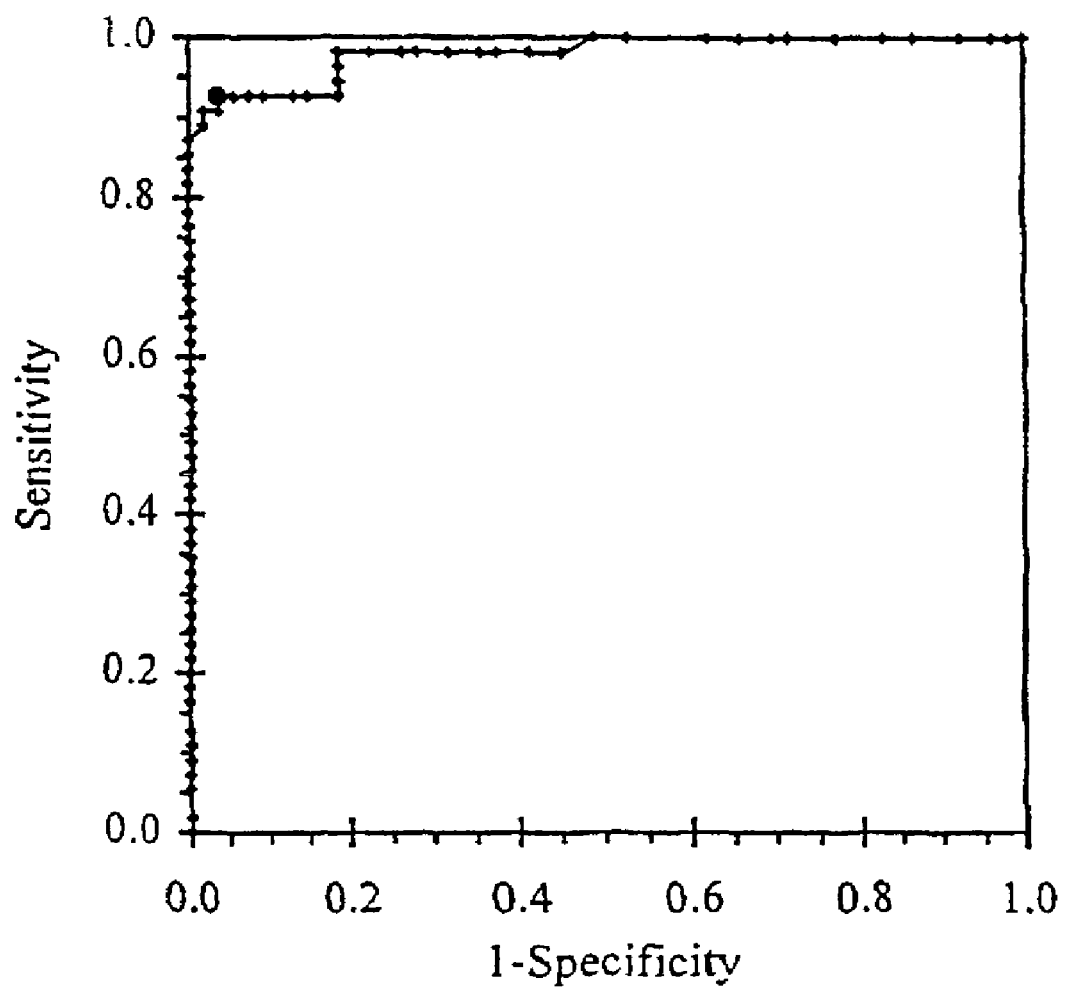
FIG. 4 ROC curve for the guinea pig TGc ELISA showing the point of greatest efficiency of the test, upon which the cut-off level was chosen.

The median of antibody concentrations for the patients with untreated GSE (CD or DH) was 51.8 AU (n=55, 95% CI: 34.2-63), for controls 8 AU (n=53, 95% CI: 7.3-8.9), the difference was significant (P<0.0001). For treated patients, the median of antibody concentrations was 18 AU (n=16, 95% CI: 9.2-69.9), for controls with gastrointestinal diseases 7.5 AU (n=26, 95% CI: 6.6-9), for healthy individuals and controls with other diagnoses 8.5 AU (n=27.95% CI: 7.2-10.3), respectively. The area under the ROC curve was 0.980 (95% CI: 0.958-1.002; 95% CI with BC, method: 0.943-0.993) (FIG. 4).

Figure 5:
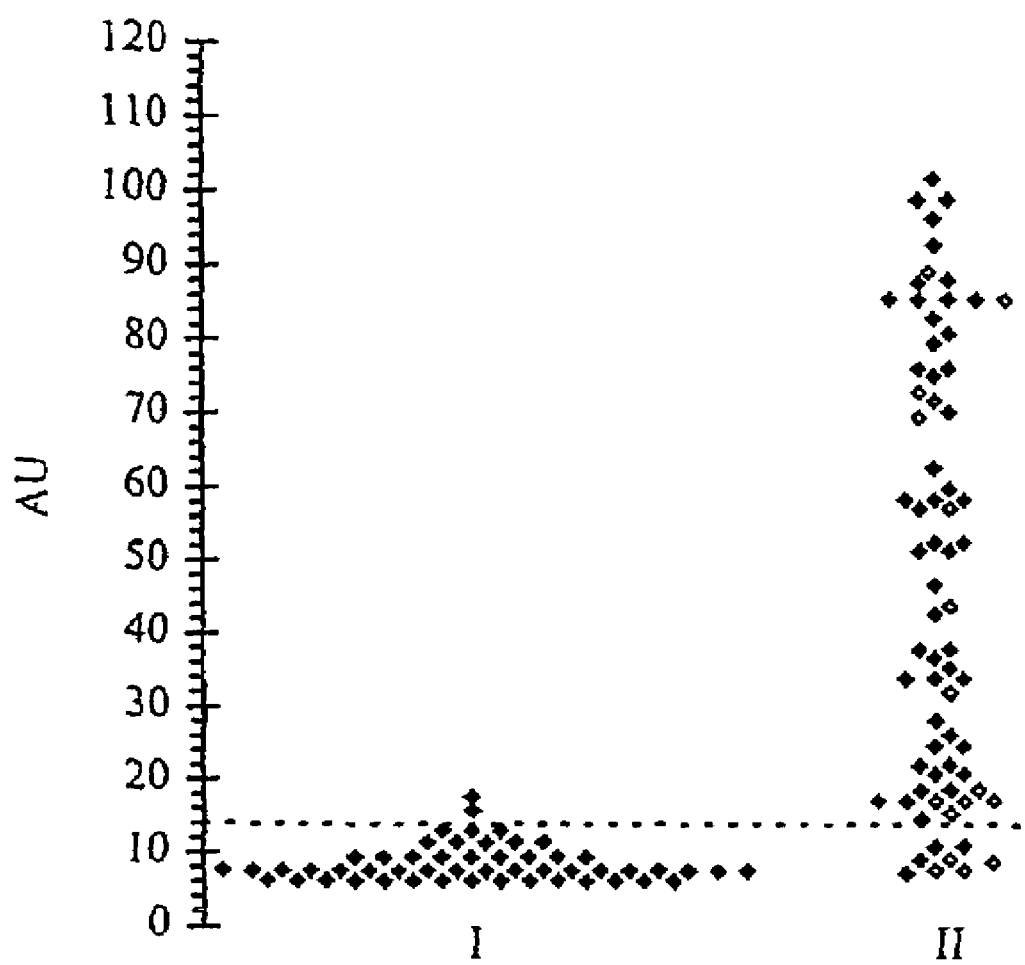
FIG. 5 Serum anti-TGc antibody concentrations in the guinea pig TGc ELISA system in the controls (I) and in the patients having CD or DH (II). Treated CD or DH patients are indicated by empty squares. The chosen arbitrary cut-off level for positivity (broken line) is drawn at the AU of 14.

A cut-off value of 14 AU was chosen, and sera with antibody concentrations equal or higher than 14 AU were labelled as guinea pig TGc ELISA positive. This cut-off value gave (excluding treated patients) a specificity and a sensitivity of 96.2% (95% CI: 92.8-99.6%) and 92.7% (95% CI: 88.1-97.3%), respectively. The coincidence of the guinea pig TGc assay with the clinical diagnosis (excluding treated patients) was 102/108 (94.4%), giving 2 false positive and 4 false negative results (FIG. 5).

Effects of Calcium-Activation.

32 serum samples were tested in ELISA for IgA anti-human TGc antibodies with and without calcium-activation. The overall antibody titres did not show significant difference (p=0.27). However, sera with anti-TGc titres lower than 30 AU in the calcium-activated assay were significantly lower in the assay without calcium-activation (n=18, p=0.009), whereas higher titres were not significantly different (n=14, p=0.35).

Comparison of EMA with TGc ELISA.

Excluding treated patients, with the exception of one false positive result, all patients with EMA positive sera had GSE (55/56, 98.2%). 12 of 16 (75%) treated patients with GSE were positive for EMA. Comparing only the untreated EMA positive cases, the results of human and guinea pig TGc ELISA coincided with the EMA test in 54/56 (96.4%) and 51/56 (91.1%) cases, respectively. The false positive serum by EMA was negative by both human and guinea pig TGc ELISAs. The one false negative serum with human TGc ELISA was also negative with guinea pig TGc ELISA. The 12 patients on incomplete gluten-free diet with EMA positivity had also positive anti-TGc IgA titres with both ELISA systems.

All patients negative for EMA were either treated patients having GSE or patients not having GSE. Comparing only the untreated EMA negative cases, the results of human and guinea pig TGc ELISA coincided with the EMA test in 52/53 (98.1%) and 51/53 (96.2%) cases, respectively. The one false positive serum with human TGc ELISA was also positive with guinea pig TGc ELISA; in addition, another false positive serum was detected by the guinea pig assay. Both false positive sera were from patients with M. Crohn. The four EMA negative patients with treated GSE were also negative by guinea pig TGc ELISA, but one of them was positive by human TGc ELISA.

The overall coincidence of EMA test with human and guinea pig ELISA was 120/124 (96.8%) and 117/124 (94.4%), respectively.

Comparison of Human TGc ELISA with Guinea Pig TGc ELISA.

The results of the two ELISAs coincided in 119/124 (96%) of all tested sera. In four discordant cases, the human assay was more sensitive than the guinea pig assay, giving positivity in the human assay. One of them was an EMA negative CD patient on gluten-free diet. In the fifth discordant case, the guinea pig ELISA gave false positive result for a patient with M. Crohn. The antibody titre was, however, also high (17.5 AU) in the human TGc ELISA, almost reaching the cut-off level (18 AU).

The false results of the human TGc ELISA coincided with those of the guinea pig TGc ELISA. Both assays failed to recognise the serum of one EMA positive CD patient, and both detected a patient having Crohn's disease as positive. Both tests gave correct, negative result in the case of a false EMA positive patient.

Figure 8:
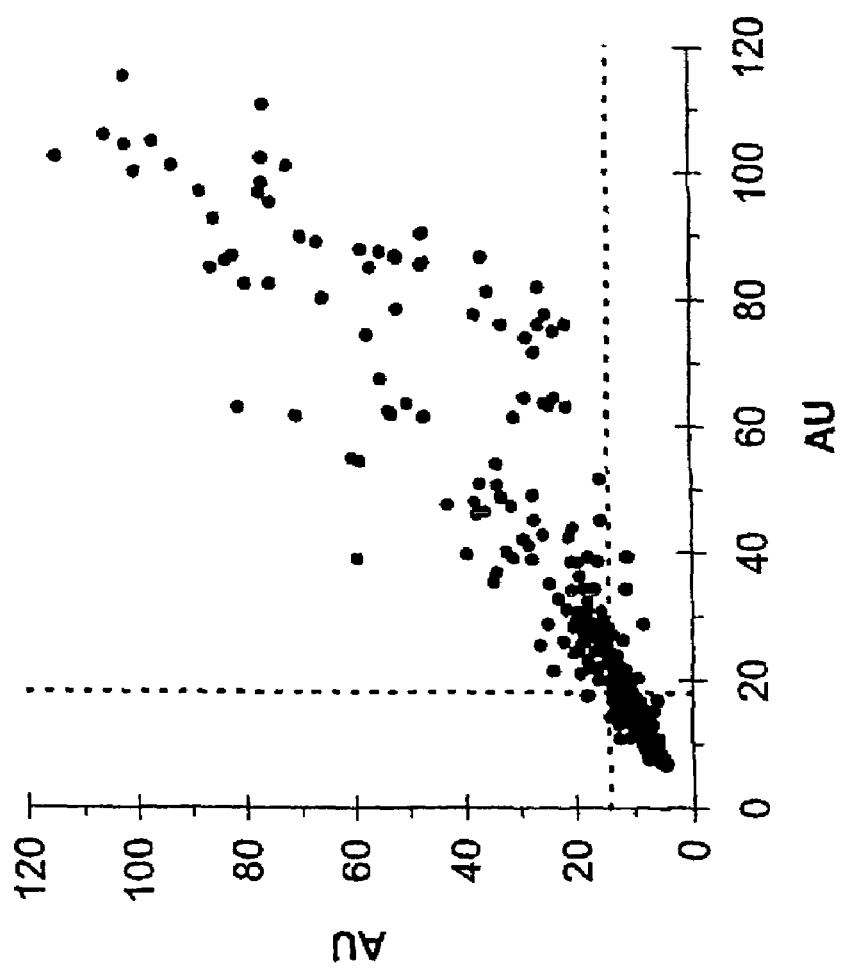
FIG. 8 Correlation of antibody titres between the human and the guinea pig TGc ELISA On the x-axis are titres given in arbitrary units measured by the human TGc ELISA, on the y-axis are those measured by the guinea pig TGc ELISA. The cut-off values are presented by dashed lines.

The titres with the two assay correlated well ($r_s$=0.9377, 95% CI: 0.9121-0.9559, p<0.0001), the correlation was theoretically exponential, but in the practice linear, with an exponent of 1.05 (FIG. 8). The difference between the areas under the ROC curves was 0.019 (95% CI: −0.002-0.040; 95% CI with $BC_a$ method: 0.005-0.056).

Recombinant Human TGe

The human TGe was expressed in the 293-EBNA human embryonic kidney cell line as a fusion proenzyme with the Strep II tag. The protein could be purified in a single step by affinity binding to a StrepTactin™ column. After elution with desthiobiotin the protein gave a single 80 kDa band in SDS-PAGE (FIG. 9), which reacted with monoclonal antibodies against the Strep II tag (FIG. 10). The column bound almost all the tagged TGe with no immunoreactivity appearing in the flow through. The yield from the lysate of a confluent cell monolayer in a cell culture dish of 13 cm diameter was approximately 200 μg. The molecular mass calculated from the sequence of the human TGe proenzyme is 76826 Da, and the calculated molecular mass of the fusion protein (TGe proenzyme having a carboxyterminal tag of 10 amino acids) is 78011 Da. Mass spectrometry of the fusion protein gave a molecular mass of 77765 Da. In cell lysates, the activity of the expressed human TGe was 2.5 times higher than the background activity of transglutaminases present in untransfected 293-EBNA cells. The freshly purified human TGe proenzyme showed 1:40-1:80 of the activity of TGc and when activated with different proteases (proteinase K, trypsin or dispase) similar or higher activity than the TGc.

DISCUSSION OF EXAMPLE AND RESULTS

To our knowledge, human TGc had not been expressed before in mammalian cells via DANN recombination methods. We preferred using human cells instead of bacteria for two reasons. First, although there is no evidence for posttranslational modifications of TGc, we can not completely exclude this possibility. Such modifications would in all probability not occur in bacteria. Second, if chaperons are needed to obtain a correct folding, these are more likely to be present in human cells.

The molecular mass of the guinea pig TGc differs only slightly (0.1 kDa) from that of the human TGc when measured by mass spectrometry, but the guinea pig TGc runs appreciably faster on SOS-PAGE than the human TGc. The TGc from human fibroblasts runs with the same speed as our fusion protein, although the difference between them is 1.2 kDa. These observations imply that the difference between the structures of the human and the guinea pig TGc is more profound than suggested by their high amino acid identity.

The human TGc as a fusion protein with the Strep II tag could be purified very effectively in one step giving one single band on a Coomassie-stained gel. The protein band could be clearly identified by immunoblot as tissue transglutaminase. Mass spectrometry gave the expected molecular size. The purified recombinant human protein had transglutaminase activity. It is not known whether the human TGc has the same catalytic activity as the guinea pig enzyme. Our purified protein had similar or higher activity as the same amount of guinea pig liver TGc. Thus we conclude that the protein we used in the assays is the purified, active, human TGc with a C-terminal Strep H tag.

The guinea pig liver TGc preparation used for testing contains other protein contaminants which are not immunoreactive with monoclonal anti-TGc antibodies. However, as it had been used successfully by other authors in its original form, we did not purify it further. It can not be excluded that immunopositivity seen in microtiter wells might in some cases be due to reactivity against contaminants.

Sulkanen and co-workers (Sulkanen S et al. Gastroenterology 1998; 115:1322-8.) demonstrate that calcium given to the coating buffer, in a concentration suitable for activation of guinea pig TGc, causes improved test performance by more specific detection of TGc by antibodies. The authors explain their observation as a conformational change occurring through calcium-activation, but after coating they remove calcium by washing and as they then use a high concentration of EDTA, so the antibody-antigen reaction occurs in the absence of calcium. Thus a conformational change is assumed to be retained by the immobilised TGc molecules after removal of calcium. Besides conformational changes, which are unlikely to become irreversible by coating, there is another possible explanation for this effect. TGc can act as its own substrate, and is able to cross-link itself to form protein complexes of high molecular weight (Birckbichler P J et al, Biochem Biophys Res Commun 1977; 78:1-7). This is likely to occur in the wells where the concentration of TGc is approximately the same as used in the activity assay. Thus not only TGc monomers, but also TGc complexes may be immobilised in the ELISA wells and this may favour the binding of antibodies giving a higher signal. In addition, cross-linked TGc complexes may reveal new antigenic epitopes, different from those of the TGc monomer. This hypothesis is supported by the observation that preincubation of CD sera with calcium-activated guinea pig TGc blocks effectively the reactivity in ELISA, but to obtain the same blocking effect with inactivated guinea pig TGc, a preincubation with a tenfold amount is needed.

Sulkanen and co-workers (Sulkanen S et al., Gastroenterology 1998; 115:1322-8) changed the original method (Dieterich W et al, Nature Medicine 1997; 3(7):797-801) not only by using calcium activation, but also changed the buffer and omitted blocking. They do not present data showing which component is responsible for the improved assay performance. We tested some positive and negative sera with and without calcium-activation of the human TGc, and could not find significant changes in the overall performance of the test. This suggests that other factors, in addition to calcium, may be important in the optimisation of the guinea pig TGc assay. However, as the optical densities of EMA positive sera with anti-TGc titres lower than 30 AU in the calcium-activated assay were significantly lower, or even negative, in the assay without calcium-activation, we use calcium also in the assay with human TGc.

The setting of the cut-off values for the ELISAs was based on the ROC-analysis of the tests. A cut-off value providing perfect separation of individuals having or not having GSE could not be found, though the coincidence with the diagnosis by biopsy is in both tests very high. The guinea pig TGc ELISA was not able to detect two untreated patients with DH and one untreated patient with CD which could be detected by the human TGc ELISA The 95% confidence intervals of sensitivities of the two ELISAs overlap, and therefore the sensitivity difference has to be confirmed by further studies, but the results affirm the assumption that in a few cases autoantibodies are directed against epitopes of human TGc not conserved in guinea pig TGc. One serum from a CD patient with clear EMA positivity was not immunoreactive in either ELISA, and the titre values were so far below the cut-off that the result is probably not due to chance. It is conceivable that TGc is not the only autoantigen in GSE, and that in some rare cases, even though EMA positivity occurs, no antibodies against TGc are present. This is supported also by the observation that the immunoabsorption of IgA-class autoantibodies against TGc by guinea pig TGc cannot completely abrogate anti-endomysium activity (Lock R J et al., Clin Exp Immunol 1999; 116:258-62), although these experiments should be repeated using the calcium-activated human TGc, as not all patients' antibodies may cross-react with the guinea pig antigen.

The EMA test gave a false positive result in an 8-year-old girl who had a transient diarrhoea in February 1998. Repeated EMA tests showed IgA binding in the intercellular spaces of smooth muscle cells. Jejunal histology was negative for GSE, and the diarrhoea has not recurred. The fact that a serum was false positive by EMA test, but correctly diagnosed by both ELISAs, also underlines the possibility of EMA positivity due to antigens other than TGc.

It is interesting that two EMA-negative patients with Crohn's disease had TGc antibody titres above the cut-off level in the guinea pig TGc ELISA, one of them also in the human TGc ELISA Coeliac disease and Crohn's disease have been described to occur in the same patient (Gillberg R et al, Scand J Gastroenterol 1982; 17:491-6), but this association is very rare. In our two cases associated coeliac disease can not be ruled out, but as both titres are near to the borderline (21.6 and 17.5 AU in the human TGc ELISA, 15.9 and 17.8 AU in the guinea pig ELISA), the elevation of titres might result from a low level IgA autoantibody production against TGc in Crohn's disease rather than from that in active coeliac disease. This speculation is supported by the fact that in both ELISA systems the median of titres of patients with Crohn's disease is greater than that of healthy individuals and patients with other gastrointestinal or non-gastrointestinal diseases. However, the differences and the number of patients' sera tested in the present study are too small to allow us to judge the significance of this finding.

Patients on complete or incomplete gluten-free diet had a wide spectrum of antibody titres, and the results of the ELISAs were in good agreement with those of EMA tests. The ELISA with the human antigen turned out to be slightly more sensitive in this regard than the EMA test or the guinea pig ELISA, recognising one EMA- and guinea pig ELISA negative CD patient as positive.

Compared to the other established systems, the human TGc ELISA was found to be as specific and sensitive as the EMA test, and somewhat superior to the guinea pig TGc ELISA. The results show the high diagnostic value of all tested systems in this study, but in particular that of the human TGc ELISA, which has almost perfect sensitivity and specificity, and does not have the disadvantages of EMA test Thus we conclude that the human TGc-based ELISA should be the method of choice for easy and non-invasive screening and diagnosis of GSE.

Figure 6:
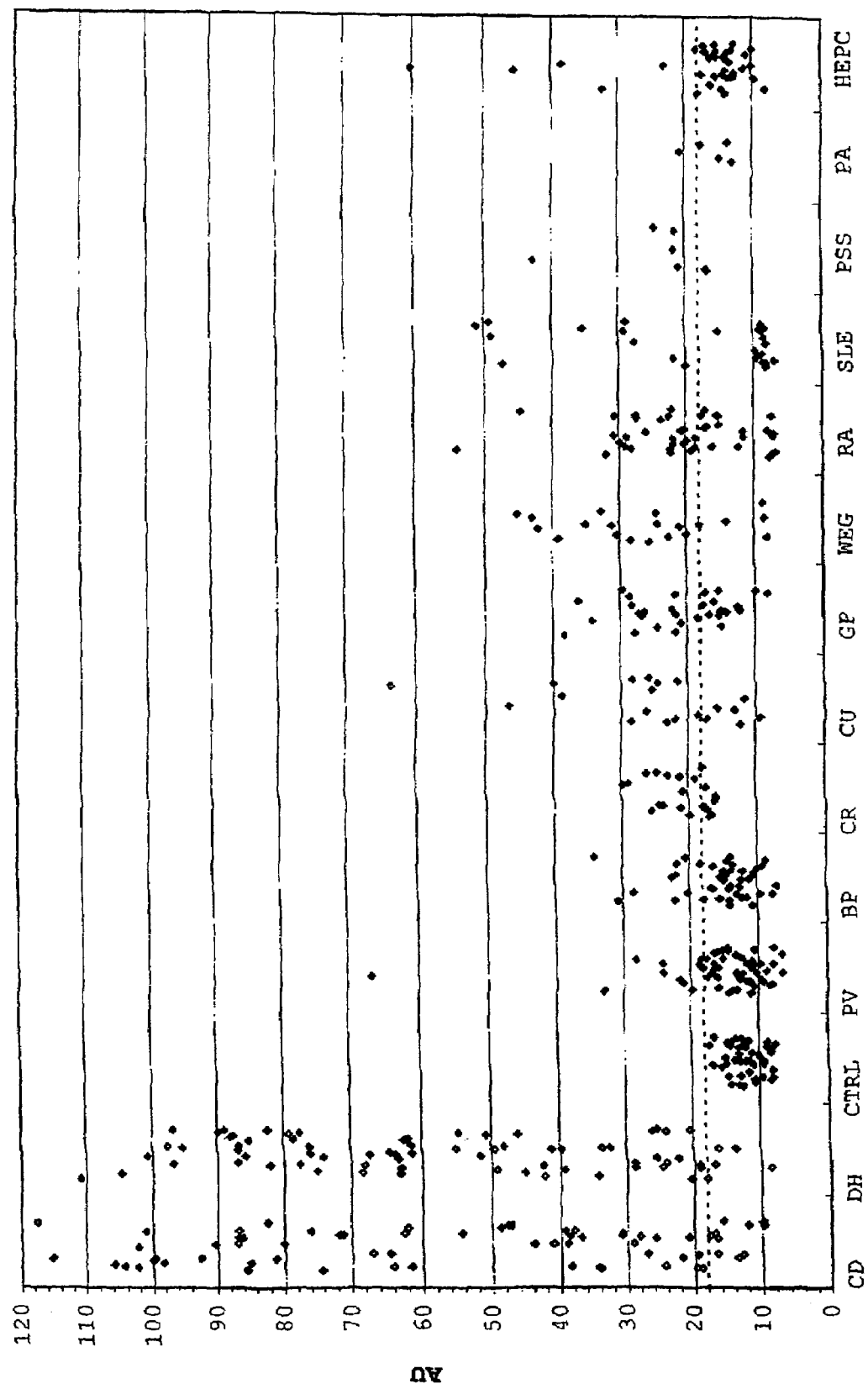
FIG. 6 Serum concentrations of IgA antibodies against TGc in the human TGc ELISA given in arbitrary units (AU). Treated CD or DH patients are indicated by empty squares. The chosen arbitrary cut-off for positivity (dashed line) is drawn at 18 AU. CD, coeliac disease; DH, dermatitis herpetiformis; CTRL, control sera; PV, pemphigus vulgaris; BP, bulbous pemphigoid; CR, Crohn disease; CU, colitis ulcerosa; GP, Goodpasture syndrome; WEG, Wegener granulamatosis; RA, rheumatoid arthritis; SLE, systemic lupus erythematosus; PSS, progressive systemic sclerosis; PA, psoriatic arthritis; HEPC, hepatitis C.
Figure 7:
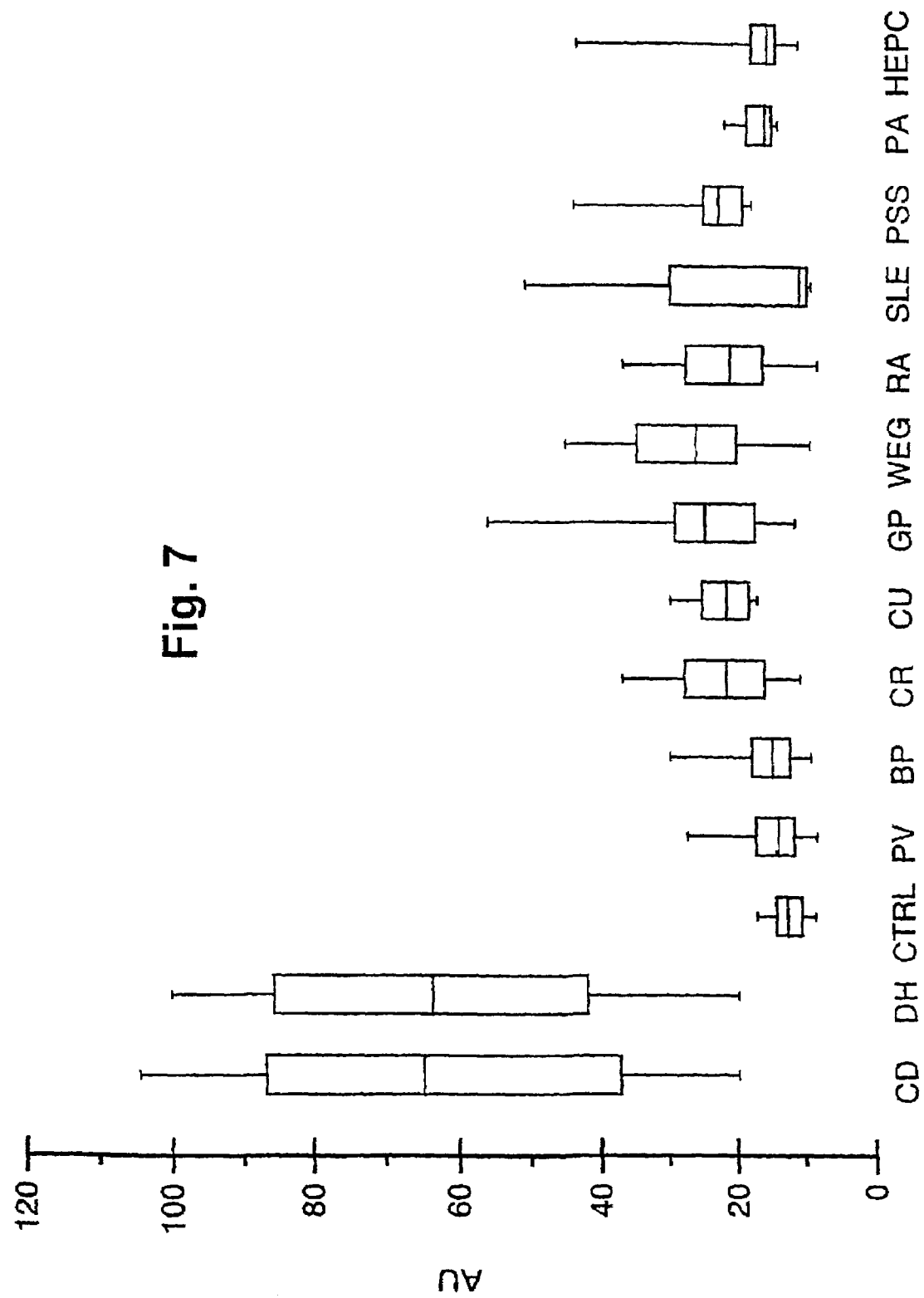
FIG. 7 Box and whisker diagram showing the serum concentrations of IgA antibodies against human TGc. The lower and upper edges of the boxes represent the 25% and 75% percentiles, respectively. The median is indicated by a horizontal line through the box. The lower and upper whiskers represent the 5% and 95% percentiles, respectively. Only untreated patients are included in the CD and DH groups. For abbreviations see FIG. 6.

The results summarised in FIGS. 6 and 7 show that IgA against human tissue transglutaminase is also detected in autoimmune disorders other than gluten sensitive enteropathy. The positivity in the human TGc ELISA among patients with autoimmune disease other than CD and DH is most probably not due to these patients having an active GSE. It is indeed very unlikely that more than the quarter of all autoimmune patients would have associated GSE, even though it is conceivable that in some cases where the titres are very high the test shows a real association. Celiac disease has been described to associate with various autoimmune disorders as shown in Table 2 below:

TABLE 2

Forms of autoimmune (AI) diseases that have been reported to associate with GSE:

| | |
|---|---|
| Addison's disease | Recurrent pericarditis |
| AI haemolytic anaemia, | Relapsing polychondritis |
| AI thrombocytopenic purpura | Rheumatoid arthritis |
| AI thyroid diseases | Sarcoidosis |
| Atrophic gastritis - pernicious anaemia | Sjögren's syndrome |
| IgA nephropathy or IgA glomerulonephritis | SLE, splenic atrophy |
| Myasthenia gravis | Type I (insulin-dependent) diabetes mellitus |
| Partial lipodystrophy | Ulcerative colitis |
| Polymyositis | Vasculitis (both systemic and cutaneous) |
| Primary biliary cirrhosis | Vitiligo |
| Primary sclerosing cholangitis | |

A part of these associations are proven, the other part have been anecdotal.

It has been known that GSE can provoke a T-cell mediated inflammation of the duodenojejunal bowel region causing various resorption disturbances (for review see Trejdosiewicz L K et al., Clin Gastr 1995; 9:251-72). The latter may result in painful diarrhea, sideropenic anemia, hypoproteinemia, osteoporosis, amenorrhea, hypovitaminoses, and in children in retardation of growth and development (for review see Corazza G R, Gasbarrini G. Coeliac disease in adults. Bailliere Clin Gastr 1995; 9:329-50; Littlewood J M. Coeliac disease in childhood. Bailliere Clin Gastr 1995; 9:295-328.). Beside these direct consequences the persistence of the disease predisposes of various autoimmune disorders (e.g. diabetes type 1), and malignancies (e.g. duodenojejunal lymphomas). The clinical signs and symptoms of DH are mainly those of skin affection (polymorphic, itching blisters with underlying erythema typically located over the extensor surfaces of the big joints), the gastroenterological symptoms are often mild or clinically completely absent. However, the inflammatory small bowel changes can often be found by histological examination even if there are no clinical signs or symptoms suggesting jejunal pathology. The enteropathy in DH is morphologically, clinically and functionally identical with that in CD suggesting identical or very similar aetiology and pathomechanism of both of these two forms of GSE.

Our results however show a general role of TGc and other transglutaminases in autoimmune processes. As a consequence positive results for TGc IgA in patients suffering from other autoimmune disease should not alone be taken as the basis for the diagnosis of GSE. On the other hand, antibodies against TGc and other transglutaminases such as TGe can be used as a marker for patients suffering from other autoimmune disease of the GSE-type and may serve to define subgroups of patients within such disease groups.

Consequently, we provided a new method for diagnosis of autoimmune diseases of the GSE-type or associated with gluten sensitive enteropathy, essentially comprising taking a specimen and testing the specimen for antibodies against human tissue transglutaminase, or other transglutaminases. In this way autoimmune diseases other than coeliac disease can be diagnosed and distinguished, notably, dermatitis herpetiformis Duhring, Addison's disease, AI haemolytic anaemia, AI thrombocytopenic purpura, AI thyroid diseases, atrophic gastritis—pernicious anaemia, IgA nephropathy or IgA glomerulonephritis, myasthenia gravis, partial lipodystrophy, polymyositis, primary billary cirrhosis, primary sclerosing cholangitis, recurrent pericarditis, relapsing polychondritis, rheumatoid arthritis, rheumatism, sarcoidosis, Sjogren's syndrome, SLE, splenic atrophy, type I (insulin-dependent) diabetes mellitus, diabetes mellitus of other types, ulcerative colitis, vasculitis (both systemic and cutaneous) vitiligo as well as autoimmune diseases associated with female infertility (Collin et al., Gut, 1996: 39, 382-384), increased risk of abortion (Smecul et al., Eur. J. Gastr. & Hep. 1996; 8(1), 63-67), or reduced fetal growth due to the presence of an autoimmune disease of the GSE-type or latent, non-active GSE.

The invention claimed is:

1. A method for diagnosing a gluten sensitive enteropathic autoimmune disease consisting of dermatitis herpetiformis and coeliac disease, comprising
   (a) taking a sample from a patient;
   (b) testing the sample for IgA antibodies against human tissue transglutaminase;
   (c) testing the sample for IgA antibodies against epidermal transglutaminase (TGe) and
   (d) correlating significantly increased amounts of the IgA antibodies specific for human tissue transglutaminase and IgA antibodies specific for epidermal transglutaminase (TGe) as compared to a control sample, with a diagnosis of the gluten sensitive enteropathic autoimmune disease, thereby diagnosing the gluten sensitive enteropathic autoimmune disease.

* * * * *

SEQUENCE LISTING

```
<160> NUMBER OF SEQ ID NOS: 16

<210> SEQ ID NO 1
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 1
ggccgcatgg agccatccac aattcgaaaa gta                                   33

<210> SEQ ID NO 2
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 2
```

```
ggcctacttt tcgaattgtg gatggctcca tgc                                 33

<210> SEQ ID NO 3
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 3
attaagcttg ccgccaccat ggccgaggag ctggtc                              36

<210> SEQ ID NO 4
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 4
taagcggccg cggggccaat gatgacattc                                     30

<210> SEQ ID NO 5
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 5
attaagcttg ccgccaccat ggctgctcta ggagtc                              36

<210> SEQ ID NO 6
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 6
attgcggccg cttcggctac atcgatggac aac                                 33

<210> SEQ ID NO 7
<211> LENGTH: 46
<212> TYPE: DNA
<213> ORGANISM: Artificial Sequence
<220> FEATURE:
<223> OTHER INFORMATION: Synthetic Oligonucleotide

<400> SEQUENCE: 7
ctagttgccg ccaccatggc ttggagccat ccacaattcg aaaagg                   46

<210> SEQ ID NO 8
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 8
ctagcgcctt ttcgaattgt ggatggctcc aagccatggt ggcggcaa                 48

<210> SEQ ID NO 9
<211> LENGTH: 31
<212> TYPE: DNA
```

```
<213> ORGANISM: Artificial Sequence
<220> FEATURE:
<223> OTHER INFORMATION: Synthetic Oligonucleotide

<400> SEQUENCE: 9
attgcggccg ccatggccca agggctagaa g                                    31

<210> SEQ ID NO 10
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 10
taagcggccg ctaatgcaaa gtctacataa ac                                   32

<210> SEQ ID NO 11
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 11
attgctagcc caagggctag aagtgg                                          26

<210> SEQ ID NO 12
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 12
taagcggccg cttataatgc aaagtctaca taaac                                35

<210> SEQ ID NO 13
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 13
attaagcttg ccgccaccat gatggatggg ccacgttcc                            39

<210> SEQ ID NO 14
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 14
attgcggccg cagctccacc tcgagatgcc atagg                                35

<210> SEQ ID NO 15
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 15
attgctagca gatgggccac gttccgatg                                       29
```

```
<210> SEQ ID NO 16
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 16
attggatcct aagctccacc tcgagatgc                              29
```